US010653420B2

(12) United States Patent
Scheib et al.

(10) Patent No.: US 10,653,420 B2
(45) Date of Patent: May 19, 2020

(54) COMPLIANT COMPENSATION FEATURES FOR END EFFECTOR OF SURGICAL STAPLING INSTRUMENT

(71) Applicant: Ethicon Endo-Surgery, LLC, Guaynabo, PR (US)

(72) Inventors: Charles J. Scheib, Loveland, OH (US); Michael J. Vendely, Lebanon, OH (US)

(73) Assignee: Ethicon LLC, Guaynabo, PR (US)

(*) Notice: Subject to any disclaimer, the term of this patent is extended or adjusted under 35 U.S.C. 154(b) by 594 days.

(21) Appl. No.: 15/133,306

(22) Filed: Apr. 20, 2016

(65) Prior Publication Data
US 2017/0303923 A1 Oct. 26, 2017

(51) Int. Cl.
*A61B 17/10* (2006.01)
*A61B 17/068* (2006.01)
(Continued)

(52) U.S. Cl.
CPC .......... *A61B 17/105* (2013.01); *A61B 17/068* (2013.01); *A61B 17/07207* (2013.01); *A61B 17/07292* (2013.01); *A61B 2017/00477* (2013.01); *A61B 2017/07214* (2013.01); *A61B 2090/064* (2016.02); *A61B 2090/065* (2016.02); *A61B 2090/0801* (2016.02); *A61B 2090/0807* (2016.02)

(58) Field of Classification Search
CPC .............................................. A61B 17/07292
See application file for complete search history.

(56) References Cited

U.S. PATENT DOCUMENTS

| 4,805,823 A | 2/1989 | Rothfuss |
| 5,415,334 A | 5/1995 | Williamson et al. |
| (Continued) | | |

FOREIGN PATENT DOCUMENTS

| EP | 1 256 317 A2 | 11/2002 |
| EP | 1 621 141 A2 | 2/2006 |
| (Continued) | | |

OTHER PUBLICATIONS

U.S. Appl. No. 14/827,856, filed Aug. 17, 2015.
(Continued)

*Primary Examiner* — Praachi M Pathak
(74) *Attorney, Agent, or Firm* — Frost Brown Todd LLC

(57) ABSTRACT

An apparatus includes a body assembly, a shaft extending distally from the body assembly, an end effector attached to the shaft, and a cartridge. The end effector includes a jaw and an anvil pivotable relative to the jaw. The cartridge includes a deck, a plurality of staples, a compressible buttress, a peripheral member, and a pinching surface. The deck has an upper surface facing toward the anvil. The staples are located within openings formed through the deck. Each staple has a pair of legs extending above the upper surface of the deck. The buttress is located on the upper surface of the deck. Portions of the legs of the staples are disposed the buttress. The peripheral member extends above the upper surface of the deck, laterally adjacent to the buttress. The pinching surface is located at a height extending above a height of the legs of the plurality of staples.

8 Claims, 22 Drawing Sheets

(51) Int. Cl.
*A61B 17/072* (2006.01)
*A61B 17/00* (2006.01)
*A61B 90/00* (2016.01)

(56) References Cited

U.S. PATENT DOCUMENTS

| | | | |
|---|---|---|---|
| 5,465,895 | A | 11/1995 | Knodel et al. |
| 5,597,107 | A | 1/1997 | Knodel et al. |
| 5,632,432 | A | 5/1997 | Schulze et al. |
| 5,673,840 | A | 10/1997 | Schulze et al. |
| 5,704,534 | A | 1/1998 | Huitema et al. |
| 5,792,135 | A | 8/1998 | Madhani et al. |
| 5,814,055 | A | 9/1998 | Knodel et al. |
| 5,817,084 | A | 10/1998 | Jensen |
| 5,878,193 | A | 3/1999 | Wang et al. |
| 6,231,565 | B1 | 5/2001 | Tovey et al. |
| 6,364,888 | B1 | 4/2002 | Niemeyer et al. |
| 6,783,524 | B2 | 8/2004 | Anderson et al. |
| 6,978,921 | B2 | 12/2005 | Shelton et al. |
| 7,000,818 | B2 | 2/2006 | Shelton et al. |
| 7,143,923 | B2 | 12/2006 | Shelton et al. |
| 7,303,108 | B2 | 12/2007 | Shelton |
| 7,367,485 | B2 | 5/2008 | Shelton et al. |
| 7,380,695 | B2 | 6/2008 | Doll et al. |
| 7,380,696 | B2 | 6/2008 | Shelton et al. |
| 7,404,508 | B2 | 7/2008 | Smith et al. |
| 7,434,715 | B2 | 10/2008 | Shelton et al. |
| 7,524,320 | B2 | 4/2009 | Tierney et al. |
| 7,691,098 | B2 | 4/2010 | Wallace et al. |
| 7,721,930 | B2 | 5/2010 | McKenna et al. |
| 7,806,891 | B2 | 10/2010 | Nowlin et al. |
| 7,950,561 | B2 | 5/2011 | Aranyi |
| 8,141,762 | B2 | 3/2012 | Bedi et al. |
| 8,210,411 | B2 | 7/2012 | Yates et al. |
| 8,371,491 | B2 | 2/2013 | Huitema et al. |
| 8,408,439 | B2 | 4/2013 | Huang et al. |
| 8,453,914 | B2 | 6/2013 | Laurent et al. |
| 8,479,969 | B2 | 7/2013 | Shelton |
| 8,573,461 | B2 | 11/2013 | Shelton et al. |
| 8,573,465 | B2 | 11/2013 | Shelton |
| 8,602,288 | B2 | 12/2013 | Shelton |
| 8,616,431 | B2 | 12/2013 | Timm et al. |
| 8,783,541 | B2 | 7/2014 | Shelton et al. |
| 8,800,838 | B2 | 8/2014 | Shelton |
| 8,801,735 | B2 | 8/2014 | Shelton et al. |
| 8,814,025 | B2 | 8/2014 | Miller et al. |
| 8,820,605 | B2 | 9/2014 | Shelton |
| 8,844,789 | B2 | 9/2014 | Shelton et al. |
| 8,899,464 | B2 | 12/2014 | Hueil et al. |
| 8,955,732 | B2 | 2/2015 | Zemlok et al. |
| 8,998,060 | B2 | 4/2015 | Bruewer et al. |
| 9,044,227 | B2 | 6/2015 | Shelton et al. |
| 9,101,359 | B2 | 8/2015 | Smith et al. |
| 9,186,142 | B2 | 11/2015 | Fanelli et al. |
| 9,198,644 | B2 | 12/2015 | Balek et al. |
| 9,211,120 | B2 | 12/2015 | Scheib et al. |
| 9,301,759 | B2 | 4/2016 | Spivey et al. |
| 9,393,018 | B2 | 7/2016 | Wang et al. |
| 9,398,911 | B2 | 7/2016 | Auld |
| 2008/0169328 | A1 | 7/2008 | Shelton |
| 2009/0206126 | A1* | 8/2009 | Huitema .......... A61B 17/07207 227/175.1 |
| 2012/0241493 | A1 | 9/2012 | Baxter et al. |
| 2013/0037596 | A1 | 2/2013 | Bear et al. |
| 2013/0062391 | A1 | 3/2013 | Boudreaux et al. |
| 2013/0068816 | A1 | 3/2013 | Vasudevan et al. |
| 2013/0075447 | A1 | 3/2013 | Weisenburgh et al. |
| 2013/0206813 | A1 | 8/2013 | Nalagatla |
| 2013/0221063 | A1* | 8/2013 | Aronhalt ............ A61B 17/0682 227/176.1 |
| 2014/0239036 | A1 | 8/2014 | Zerkle et al. |
| 2014/0239037 | A1 | 8/2014 | Boudreaux et al. |
| 2014/0239038 | A1 | 8/2014 | Leimbach et al. |
| 2014/0239040 | A1 | 8/2014 | Fanelli et al. |
| 2014/0239041 | A1 | 8/2014 | Zerkle et al. |
| 2014/0239042 | A1 | 8/2014 | Simms et al. |
| 2014/0239043 | A1 | 8/2014 | Simms et al. |
| 2014/0239044 | A1 | 8/2014 | Hoffman |
| 2014/0263563 | A1 | 9/2014 | Stokes et al. |
| 2015/0272575 | A1 | 10/2015 | Leimbach et al. |
| 2015/0296297 | A1 | 10/2015 | Hua et al. |
| 2015/0351754 | A1 | 12/2015 | Harris et al. |
| 2015/0351758 | A1 | 12/2015 | Shelton et al. |
| 2015/0351763 | A1 | 12/2015 | Shelton et al. |
| 2015/0351764 | A1* | 12/2015 | Shelton, IV ...... A61B 17/00491 227/176.1 |
| 2015/0374360 | A1 | 12/2015 | Scheib et al. |
| 2015/0374373 | A1 | 12/2015 | Rector et al. |
| 2016/0089146 | A1 | 3/2016 | Harris et al. |
| 2016/0278774 | A1 | 9/2016 | Shelton, IV et al. |

FOREIGN PATENT DOCUMENTS

| | | |
|---|---|---|
| EP | 1 994 890 A1 | 11/2008 |
| EP | 2 005 895 A2 | 12/2008 |
| EP | 2 604 197 A2 | 6/2013 |
| EP | 2 730 235 A1 | 5/2014 |
| EP | 2 786 718 A2 | 10/2014 |
| WO | WO 03/090630 A2 | 11/2003 |
| WO | WO 2008/057281 A2 | 5/2008 |
| WO | WO 2013/043726 A2 | 3/2013 |

OTHER PUBLICATIONS

U.S. Appl. No. 14/840,613, filed Aug. 31, 2015.
U.S. Appl. No. 14/871,071, filed Sep. 30, 2015.
U.S. Appl. No. 14/871,131, filed Sep. 30, 2015.
European Search Report, Partial, and Provisional Written Opinion dated Aug. 25, 2017 for Application No. Ep 17167143.1, 18 pgs.
European Search Report and Written Opinion dated Nov. 29, 2017 for Application No. EP 17167143.1, 17 pgs.
International Search Report and Written Opinion dated Jan. 2, 2018 for Application No. PCT/US2017/027937, 21 pgs.

\* cited by examiner

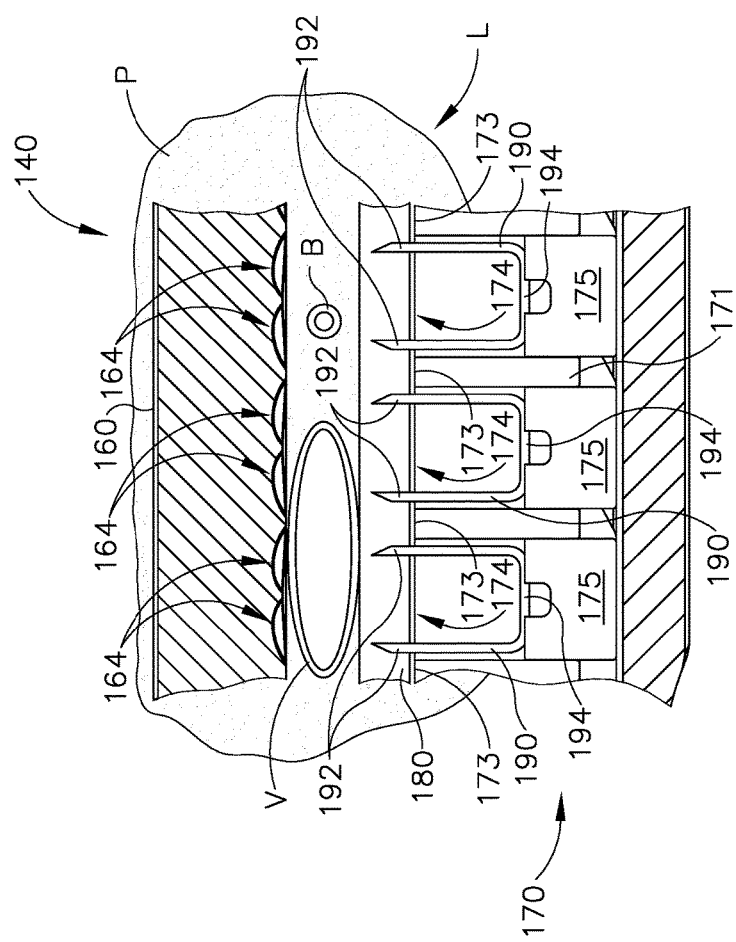

COMPLIANT COMPENSATION FEATURES FOR END EFFECTOR OF SURGICAL STAPLING INSTRUMENT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, issued as U.S. Pat. No. 9,597,082 on Mar. 21, 2017; U.S. Pub. No. 2014/0246473, entitled "Rotary Powered Surgical Instruments with Multiple Degrees of Freedom," published Sep. 4, 2014, issued as U.S. Pat. No. 9,398,911 on Jul. 26, 2016; U.S. Pub. No. 2013/0206813, entitled "Linear Stapler," published Aug. 15, 2013, now abandoned, U.S. Pub. No. 2008/0169328, entitled "Buttress Material for Use with a Surgical Stapler," published Jul. 17, 2008, now abandoned, U.S. patent application Ser. No. 14/300,804, entitled "Woven and Fibrous Materials for Reinforcing a Staple Line," filed Jun. 10, 2014, issued as U.S. Pat. No. 9,848,871 on Dec. 26, 2017; U.S. patent application Ser. No. 14/300,811, entitled "Devices and Methods for Sealing Staples in Tissue", issued as U.S. Pat. No. 9,936,954 on Apr. 10, 2018; and U.S. patent application Ser. No. 14/498,070, entitled "Radically Expandable Staple Line" filed Sep. 26, 2014, issued as U.S. Pat. No. 10,426,476 on Oct. 1, 2019. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 7B depicts a side cross-sectional view of the end effector of FIG. 4, where the end effector is in a closed position after pinching through parenchyma tissue of a liver;

Figure 1:
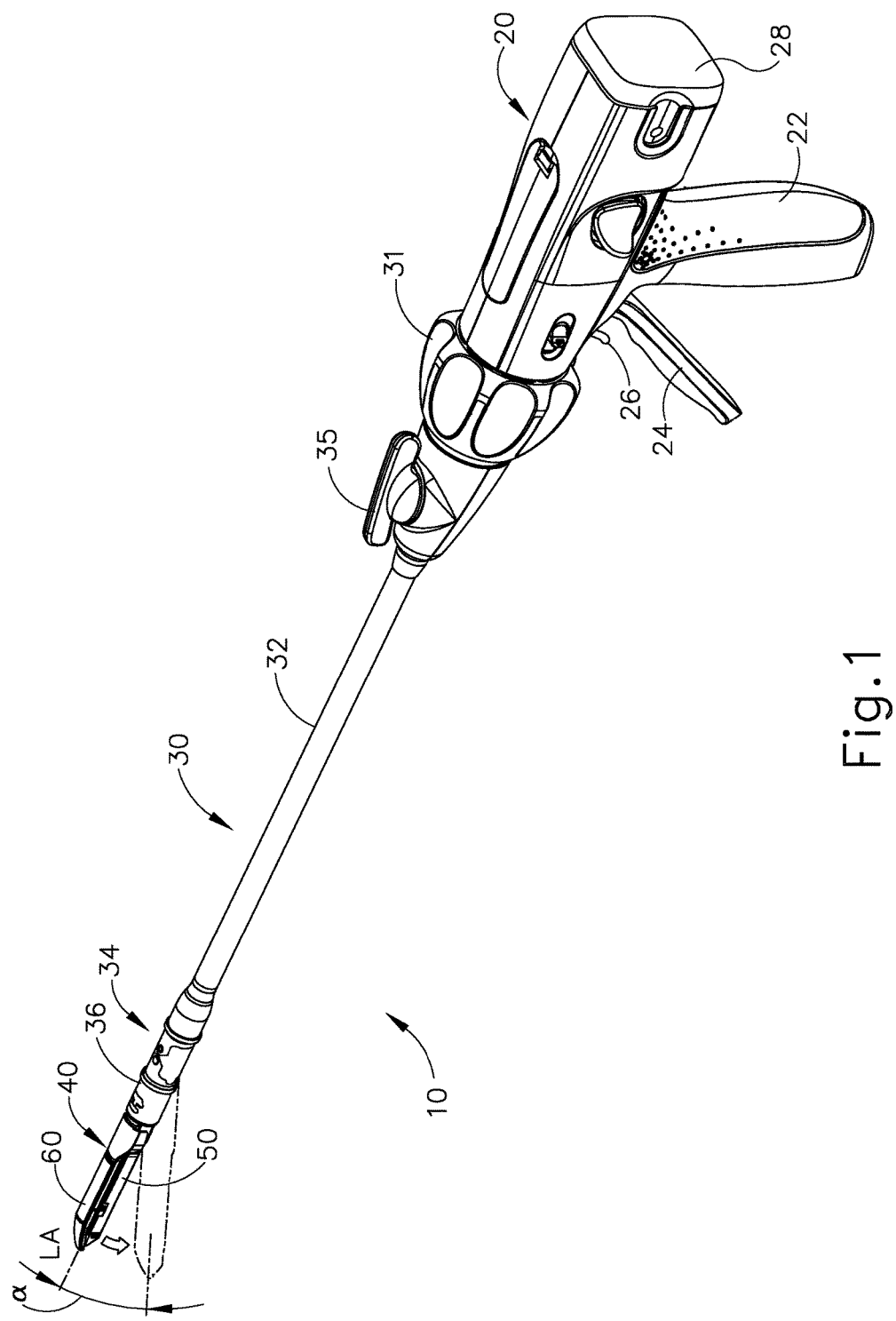
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
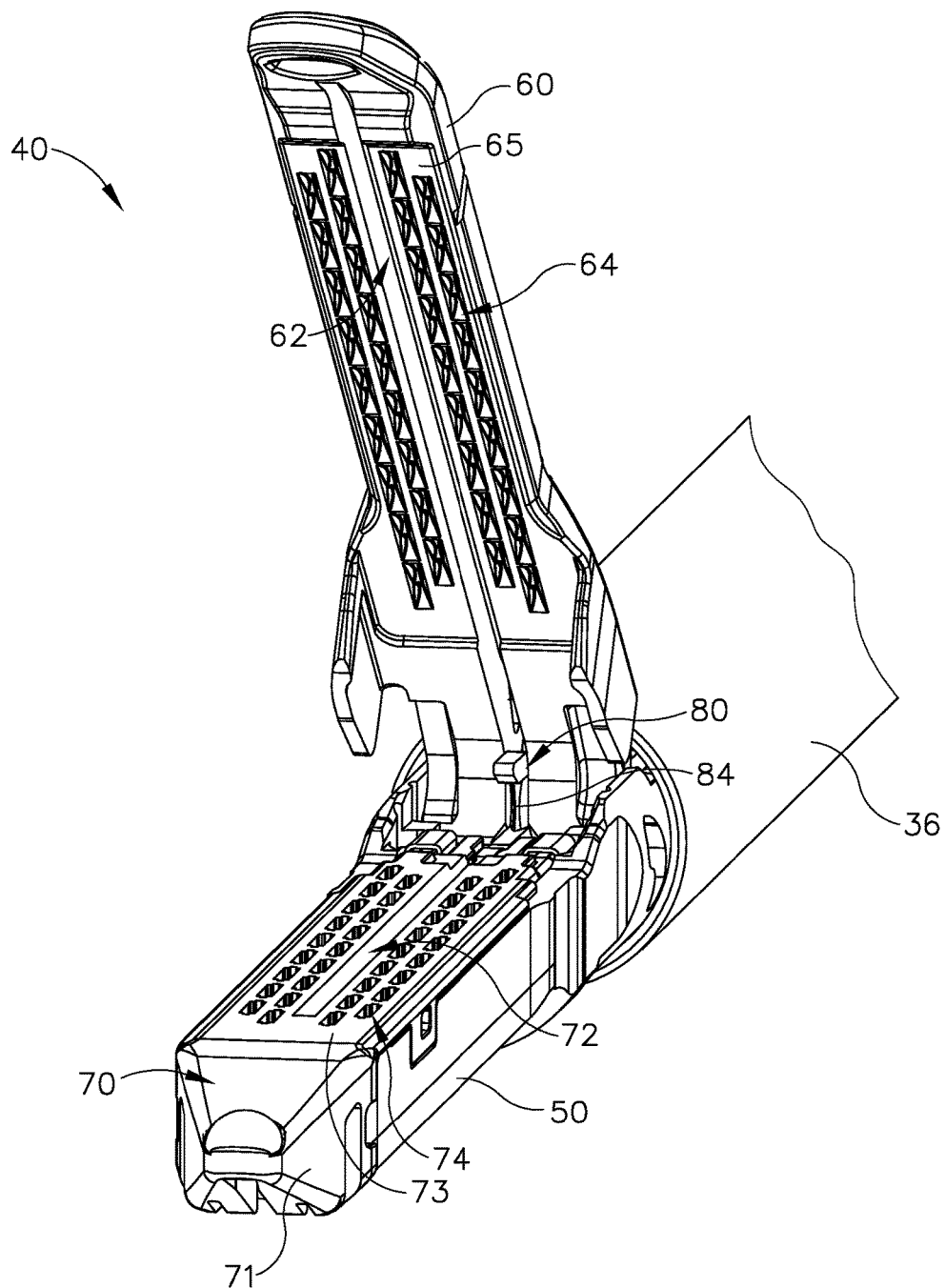
FIG. 2 depicts a perspective view of an end effector of the instrument of FIG. 1, with the end effector in an open configuration.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (α). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein; and/or U.S. patent application Ser. No. 14/314,125, entitled "Articulation Drive Features for Surgical Stapler," filed Jun. 25, 2014, issued as U.S. Pat. No. 10,292,701 on May 21, 2019, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
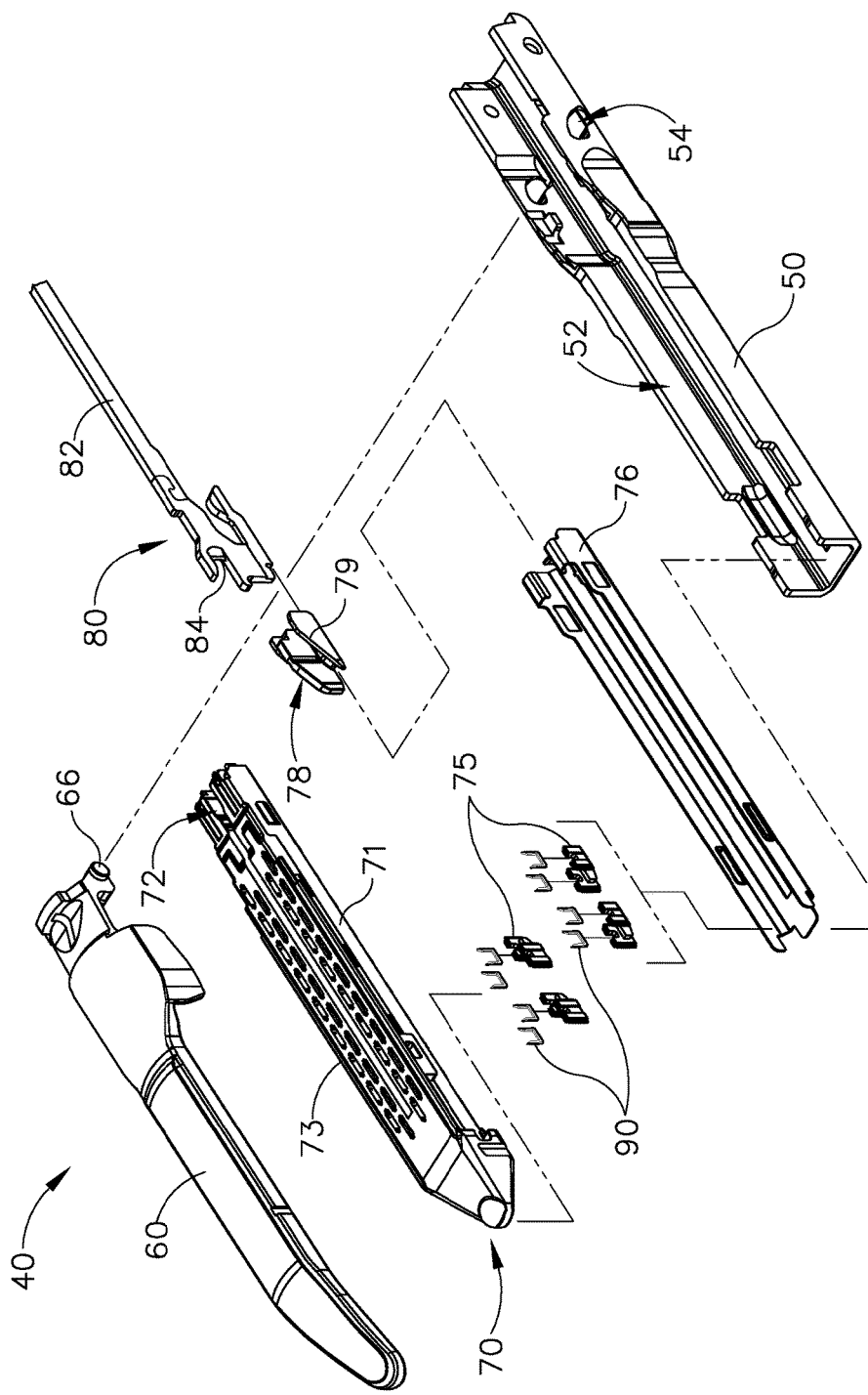
FIG. 3 depicts an exploded perspective view of the end effector of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 31, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 31, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

In the present example, a knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. Pub. No. 2015/0374373, entitled "Jaw Opening Feature for Surgical Stapler," published Dec. 31, 2015, issued as U.S. Pat. No. 10,335,147 on Jul. 2, 2019, the disclosure of which is incorporated by reference herein.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein.; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. Pub. No. 2015/0272575, entitled "Surgical Instrument Comprising a Sensor System," published Oct. 1, 2015, issued as U.S. Pat. No. 9,913,642 on Mar. 13, 2018, the disclosure of which is incorporated by reference herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary End Effectors with Buttress for Surgical Stapler

In some instances, it may be desirable to equip end effector (40) with a buttress material and/or other kind of adjunct(s). Such a buttress material and/or other kind of adjunct(s) may serve a variety of purposes, including but not limited to reinforcing the mechanical fastening of tissue provided by staples (90). Such a buttress may prevent the applied staples (90) from pulling through the tissue and may otherwise reduce a risk of tissue tearing at or near the site of applied staples (90). In addition to or as an alternative to providing structural support and integrity to a line of staples (90), a buttress and/or other adjunct(s) may provide various other kinds of effects such as spacing or gap-filling (e.g., taking up gaps otherwise formed by uneven anatomical surfaces, to promote substantially even compression forces across the length and width of end effector (40)), administration of therapeutic agents (e.g., to promote hemostasis in tissue engaged by end effector (40)), and/or other effects. While the term "buttress" will be used throughout the following discussion, it should be understood that the use of the term "buttress" is not intended to place any limitation on the functionality of the buttress. The term "buttress" should therefore be read as applying to any structure that provides an adjunct to end effector (40), serving any suitable functional purpose with respect to the tissue engaged by end effector (40).

In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various ways in which a buttress may be secured to a staple cartridge (70) or an anvil (60) will also be described in greater detail below.

It should be understood that the buttresses described below may be constructed and operable in accordance with at least some of the teachings of U.S. Pat. No. 9,044,227, entitled "Collapsible Fastener Cartridge," issued Jun. 2, 2015, the disclosure of which is incorporated by reference herein; U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Patent Pub. No. 2013/0062391, entitled "Surgical Instrument with Fluid Fillable Buttress," published Mar. 14, 2013, issued as U.S. Pat. No. 9,999,408 on Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, issued as U.S. Pat. No. 8,814,025 on Aug. 26, 2014, the disclosure of which is incorporated by reference herein; U.S. Patent Pub. No. 2013/0082086, entitled "Attachment of Surgical Staple Buttress to Cartridge," published Apr. 4, 2013, issued as U.S. Pat. No. 8,899,464 on Dec. 2, 2014, the disclosure of which is incorporated by reference herein; U.S. Patent Pub. No. 2013/0037596, entitled "Device for Applying Adjunct in Endoscopic Procedure," published Feb. 14, 2013, issued as U.S. Pat. No. 9,492,170 on Nov. 15, 2016, the disclosure of which is incorporated by reference herein; U.S. Patent Pub. No. 2013/0062393, entitled "Resistive Heated Surgical Staple Cartridge with Phase Change Sealant," published Mar. 14, 2013, issued as U.S. Pat. No. 8,998,060 on Apr. 7, 2015, the disclosure of which is incorporated by reference herein; U.S. Patent Pub. No. 2013/0075446, entitled "Surgical Staple Assembly with Hemostatic Feature," published Mar. 28, 2013, issued as U.S. Pat. No. 9,393,018 on Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, issued as U.S. Pat. No. 9,101,359 on Aug. 11, 2015, the disclosure of which is incorporated by reference herein; U.S. Patent Pub. No. 2013/0075445, entitled "Anvil Cartridge for Surgical Fastening Device," published Mar. 28, 2013, issued as U.S. Pat. No. 9,198,644 on Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; U.S. Patent Pub. No. 2013/0256367, entitled "Tissue Thickness Compensator Comprising a Plurality of Medicaments," published Oct. 3, 2013, issued as U.S. Pat. No. 9,211,120 on Dec. 15, 2015, the disclosure of which is incorporated by reference herein; U.S. patent application Ser. No. 14/300,954, entitled "Adjunct Materials and Methods of Using Same in Surgical Methods for Tissue Sealing," filed Jun. 10, 2014, issued as U.S. Pat. No. 10,172,611 on Jan. 8, 2019, the disclosure of which is incorporated by reference herein; U.S. patent application Ser. No. 14/667, 842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein; U.S. patent application Ser. No. 14/827,856, entitled "Implantable Layers for a Surgical Instrument," filed Aug. 17, 2015, published as U.S. Pub. No. 2017/0049444 on Feb. 23, 2017, the disclosure of which is incorporated by reference herein; U.S. patent application Ser. No. 14/840,613, entitled "Drug Eluting Adjuncts and Methods of Using Drug Eluting Adjuncts," filed Aug. 31, 2015, published as U.S. Pub. No. 2017/0055986 on Mar. 2, 2017, the disclosure of which is incorporated by reference herein; U.S. patent application Ser. No. 14/871,071, entitled "Compressible Adjunct with Crossing Spacer Fibers," filed Sep. 30, 2015, issued as U.S. Pat. No. 10,433,846 on Oct. 8, 2019, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein. Alternatively, the buttresses described below may be constructed and operable in any other suitable fashion.

A. Exemplary End Effector With Buttress Attached to Staples

Figure 4:
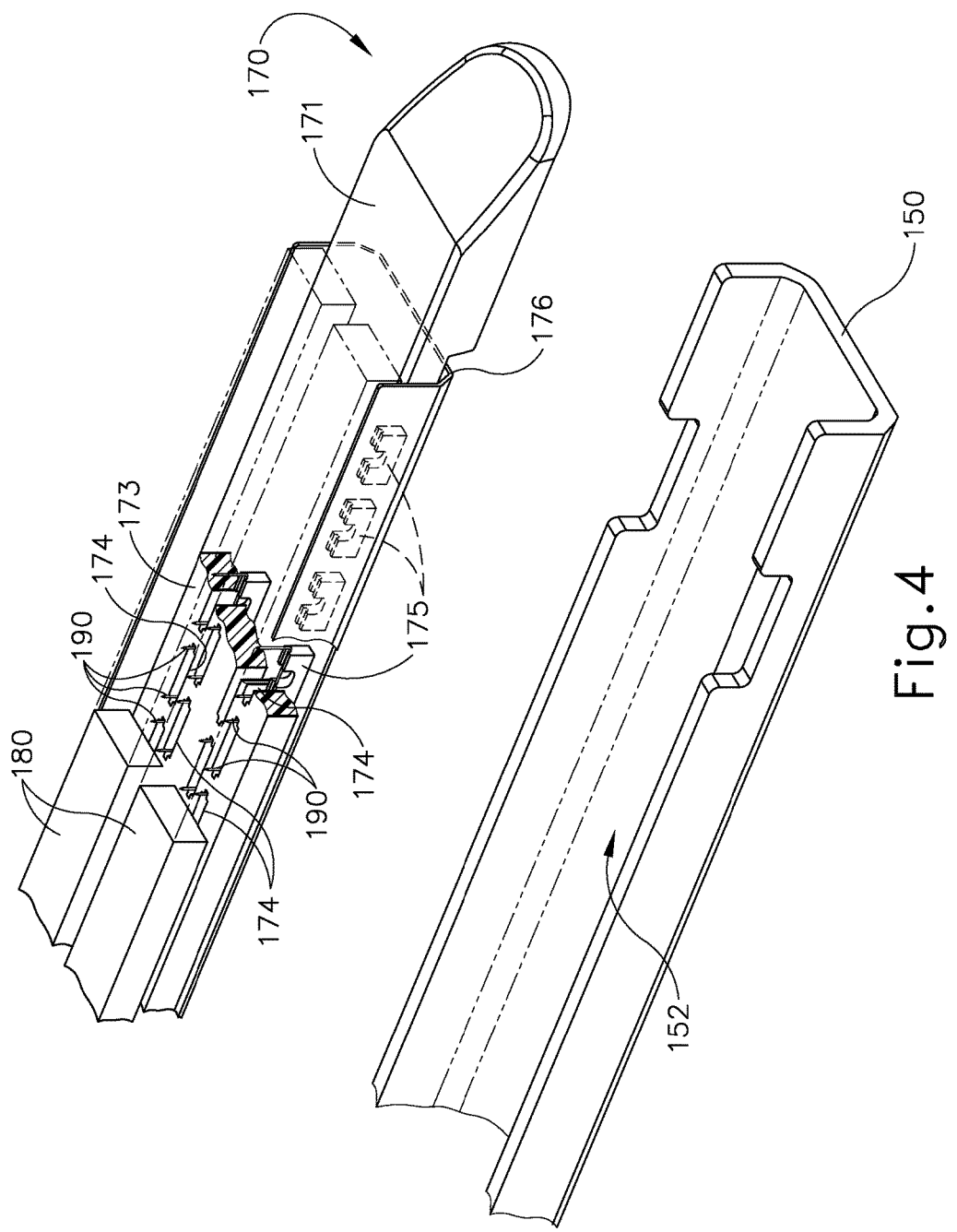
FIG. 4 depicts a perspective view of a selected portion of an exemplary end effector that may be readily incorporated into the instrument of FIG. 1.
Figure 5:
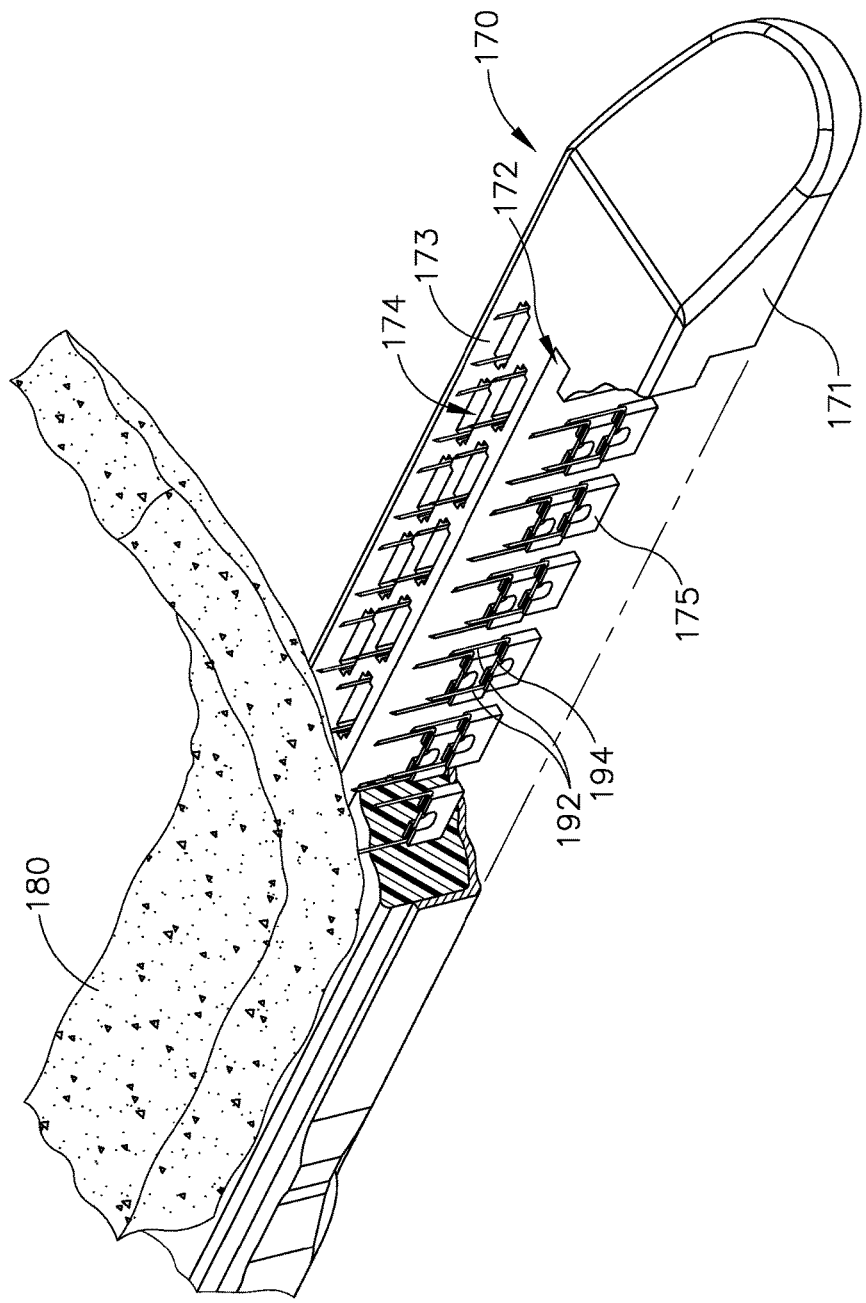
FIG. 5 depicts a partial cutaway perspective view of a selected portion of the end effector of FIG. 4.
Figure 6:
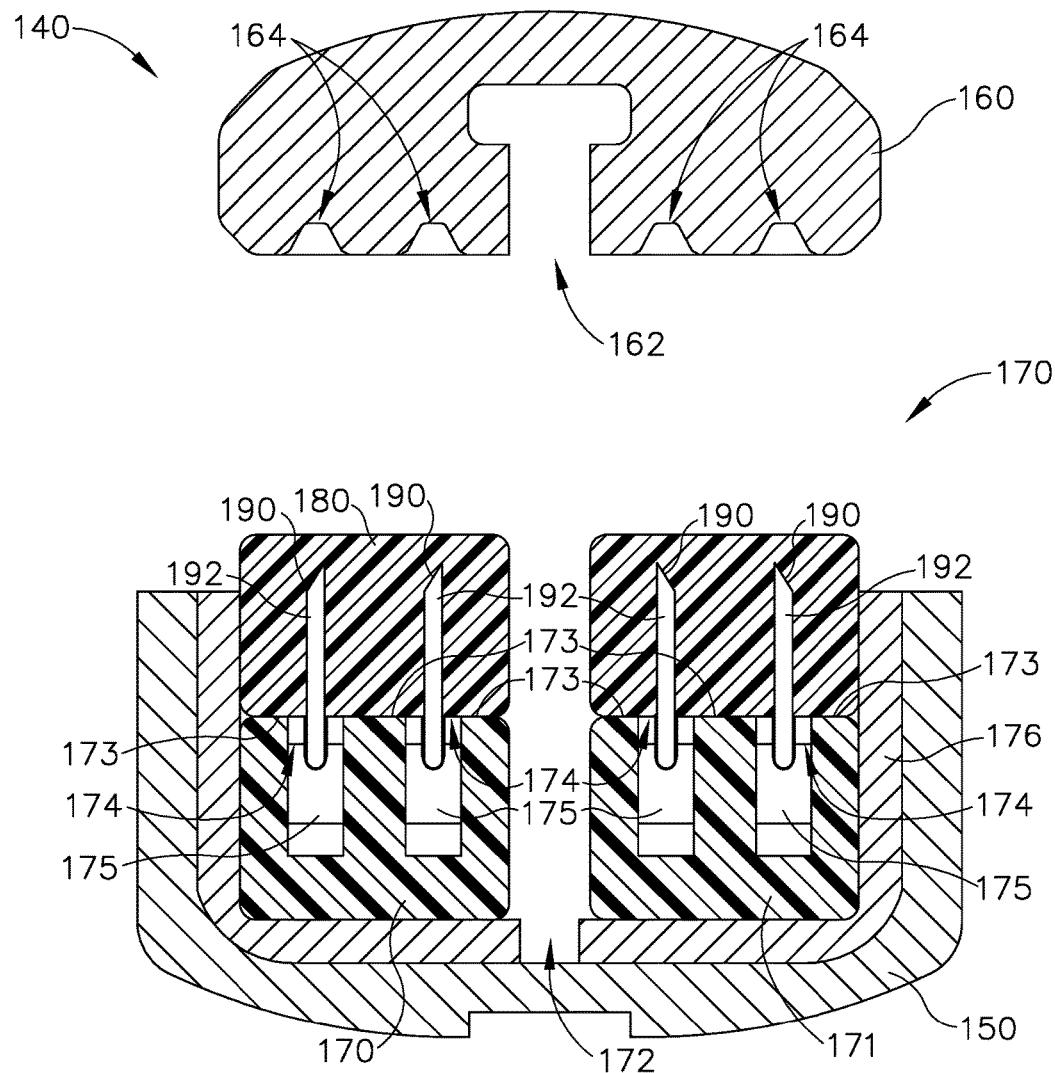
FIG. 6 depicts a front cross-sectional view of the end effector of FIG. 4.

FIGS. 4-7B show an exemplary end effector (140) that may be incorporated into instrument (10). As best seen in FIG. 6, end effector (140) includes a lower jaw (150), an anvil (160), and a staple cartridge (170). It should be understood that while end effector (140) does not specifically show knife member (80) or wedge sled (78), end effector (140) may be configured to work with knife member (80) and wedge sled (78) of end effector (40) described above. Lower jaw (150), anvil (160), and cartridge (170) are substantially similar to lower jaw (50), anvil (60), and cartridge (70) mentioned above, with differences described below. Therefore, anvil (160) is pivotable toward and away from lower jaw (150) between an open position and a closed position. It should also be understood that some versions of staple cartridge (170) may be configured to be fully compatible with end effector (40) described above, such that cartridge (170) may fit in lower jaw (50) and be used with anvil (60).

As best seen in FIG. 4, lower jaw (150) of the present example defines a channel (152) that is configured to receive staple cartridge (170). Staple cartridge (170) may be inserted into channel (152), end effector (140) may be actuated, and then staple cartridge (170) may be removed and replaced with another staple cartridge (170). Lower jaw (150) thus releasably retains staple cartridge (170) in alignment with anvil (160) for actuation of end effector (140). It should also be understood that some versions of staple cartridge (170) may be configured to be fully compatible with end effector (40) described above, such that cartridge (170) may fit in lower jaw (50) and be used with anvil (60).

Staple cartridge (170) of the present example comprises a cartridge body (171) and a tray (176) secured to the underside of cartridge body (171). The upper side of cartridge body (171) presents a deck (173) defining a plurality of staple pockets (174). A staple (190) is positioned within each staple pocket (174). As best seen in FIG. 5, each staple (190) includes a crown (194) extending between a pair of legs (192). As shown in FIGS. 4-5, legs (192) of staples (190) are dimensioned to extend from crown (194) within each corresponding staple pocket (174) and terminate above deck (173). The free ends of legs (192) thus protrude from deck (173). A compressible buttress (180) is positioned on top of deck (173). The exposed free ends of legs (192) penetrate compressible buttress (180), thereby securing compressible buttress (180) to staples (190). Compressible buttress (180) may be made out of a resilient material such that if an object, such as a vein or bile duct, is pressed against compressible buttress (180) to compress the surface of buttress (180), compressible buttress (180) would apply a reactionary force against the object due to the resilient nature of compressible buttress (180). It should be understood that legs (192) of staple (190) do not receive such a reactionary force due to the fact the free ends of legs (192) penetrate the surface of compressible buttress (180) rather than compress the surface of buttress (180).

A staple driver (175) is also positioned in each staple pocket (174), underneath a corresponding crown (194) of each staple (190), and above tray (176). Similar to staple drivers (75) described above, staple drivers (175) are operable to translate upwardly in staple pockets (174) to thereby drive staples (190) upwardly through staple pockets (174) and into engagement with anvil (160). In particular, horizontal translation of wedge sled (78) leads to vertical translation of staple drivers (175), similar to how wedge sled (78) interacts with staple drivers (75) mentioned above.

Anvil (160) of the present example comprises a longitudinally extending channel (162), a plurality of staple forming pockets (164), and lateral edges (166). As will be described in greater detail below, lateral edges (166) may provide a pinching force against soft tissue, such as parenchyma, when anvil (160) pivots from an open position to a closed position and soft tissue is between anvil (160) and compressible buttress (180).

Channel (162) is configured to align with channel (172) of staple cartridge (170) when anvil (160) is in a closed position. Aligned channels (162, 172) may receive knife member (80). Each staple forming pocket (164) is positioned to lie over a corresponding staple pocket (174) of staple cartridge (170) when anvil (160) is in a closed position. Staple forming pockets (164) are configured to deform the legs (192) of staples (190) when staples (190) are driven through tissue and into anvil (160). In particular, staple forming pockets (164) are configured to bend the legs (192) of staples (190) to secure the formed staples (190) in the tissue. Staples (190) and compressible buttress (180) are dimensioned such that as staples (190) are driven against anvil (160) to bend legs (192) of staples (190), crowns (194) and legs (192) of staples (190) are still associated with compressible buttress (180). Therefore, after staple cartridge (170) is actuated, compressible buttress (180) remains with the staple line formed by staples (190).

Knife member (80) may be positioned within channels (162, 172) of anvil (160) and staple cartridge (170). Additionally, distal longitudinal translation of knife member (80) may also drive wedge sled (78) in the distal longitudinal direction in order to drive staples (190) in the vertical direction toward anvil (160). Therefore, distally presented cutting edge (84) of knife member (80) may sever tissue located within channels (162, 172) while wedge sledge (78) drives staples (190) against anvil (160) so that staples (190) are driven through tissue adjacent to channels (162, 172). While end effector (140) of the present example has two strips of buttress (180) positioned on each side of channel (172), some other versions may have just a single strip of buttress (180) spanning across channel (172), extending across the full width of deck (173). In such versions, cutting edge (84) may also cut through buttress (180) as cutting edge (84) cuts through tissue.

Figure 7A:
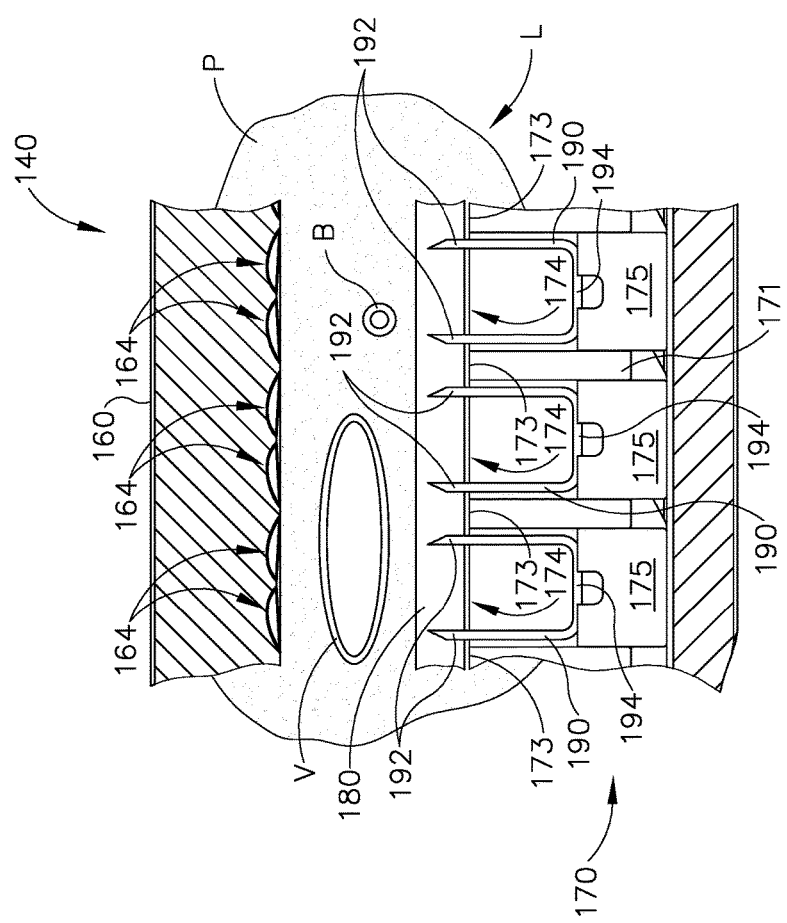
FIG. 7A depicts a side cross-sectional view of the end effector of FIG. 4, where the end effector is in an open position pinching through parenchyma tissue of a liver.
Figure 7C:
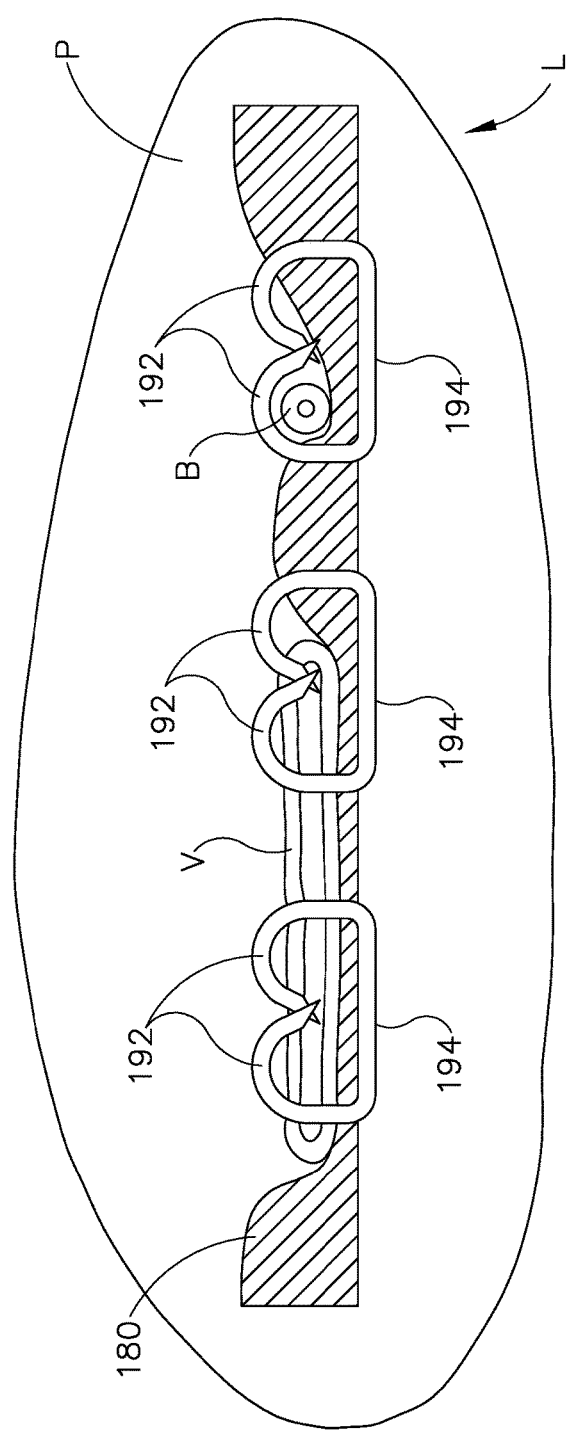
FIG. 7C depicts a side cross-sectional view of a staple line created by the end effector of FIG. 4, after the end effector pinched through parenchyma tissue of a liver and severed and stapled a vessel and bile duct having different cross-sectional areas.

FIGS. 7A-7C show a sequence where end effector (140) transitions from an open configuration to a closed configuration while compressing a liver (L) thereby pinching parenchyma (P), and then cutting and sealing a vein (V) and bile duct (B). In particular, FIG. 7A shows parenchyma (P), vein (V), a bile duct (B) positioned between anvil (160) and staple cartridge (170), with anvil (160) in the open position. Next, trigger (24) is pivoted toward pistol grip (22) to drive closure tube (32) and closure ring (36) distally. This drives anvil (160) to the closed position as shown in FIG. 7B. It should be understood that as anvil (160) closes, lateral edges (166) impart a pinching force on parenchyma (P) of liver (L). This pinching force provides dissection of the parenchyma (P). However, the pinching force does not dissect vein (V) or bile duct (B).

At this stage, vein (V) is in contact with both anvil (160) and compressible buttress (180). However, bile duct (B) is not in contact with anvil (160) or compressible buttress (180). End effector (140) is then actuated as described above, which causes knife member (80) to sever vein (V) and bile duct (B) while wedge sledge (78) drives legs (192) of staples (190) through compressible buttress (180), and portions of vein (V). As shown in FIG. 7C, crowns (194) of driven staples (190) capture and retain compressible buttress (180) against both vein (V) and bile duct (B). Conversely, free ends of deformed legs (192) of staples (190) capture and retain both vein (V) and bile duct (B) against compressible buttress (180). Because vein (V) and bile duct (B) have different cross-sectional dimensions, vein (V) and bile duct (B) compress the surface of compressible buttress (180) at different thicknesses. However, staples (190) and compressible buttress (180) cooperate to sufficiently compress against the severed open ends of vein (V) and bile duct (B) to effectively seal the open ends of vein (V) and bile duct (B).

While end effector (140) is used on a liver (L) in the present example, it should be understood that end effector (140) may be used on any other suitable anatomical structure(s) as would be apparent to one having ordinary skill in the art in view of the teachings herein.

B. Exemplary End Effector with Peripheral Pinching Cartridge

As mentioned above, anvil (160) may provide a pinching force against soft tissue when anvil (160) pivots from an open position to a closed position and soft tissue is located between anvil (160) and compressible buttress (180). Additionally, as mentioned above, compressible buttress (180) is attached to staple cartridge (170) because the free ends of staple legs (192) extending from staple deck (173) penetrate compressible buttress (180). The pinching force provided by the closure of anvil (160) toward compressible buttress (180) may inadvertently cause soft tissue to compress the top surface of compressible buttress (180), thereby exposing the free ends of staple legs (192) past the top surface of compressible buttress (180). If staple legs (192) are exposed above the top surface of compressible buttress (180), staple legs (192) may inadvertently snag on soft tissue, parenchyma, veins, or bile ducts before staples (190) are intentionally fired against anvil (160). Therefore, it may be desirable to provide an end effector that helps prevent compressing of buttress (180) in response to anvil (160) pinching soft tissue, thereby preventing the exposed free ends of staple legs (192) from undesirably snagging on tissue during closure of end effector (140).

Figure 8:
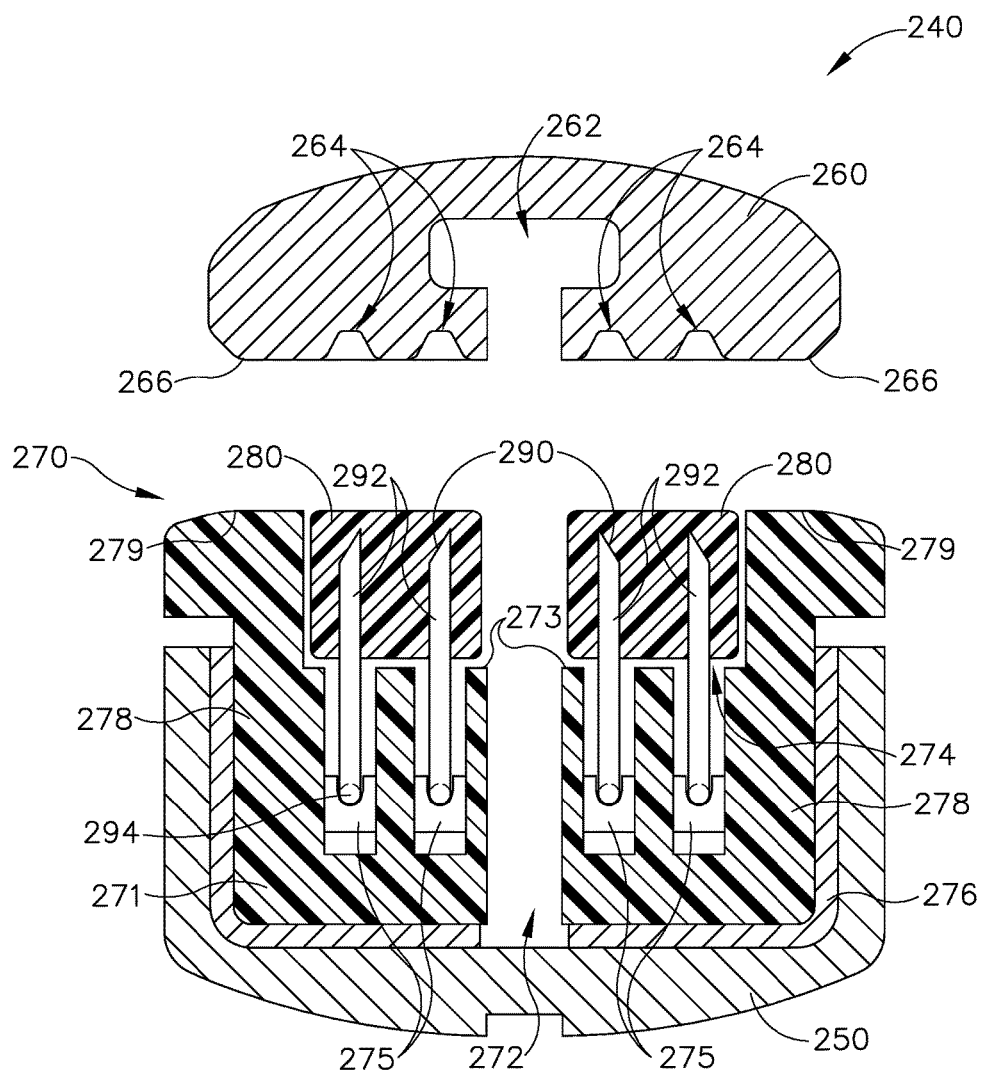
FIG. 8 depicts a front cross-sectional view of another exemplary end effector that may be readily incorporated into the instrument of FIG. 1.
Figure 9A:
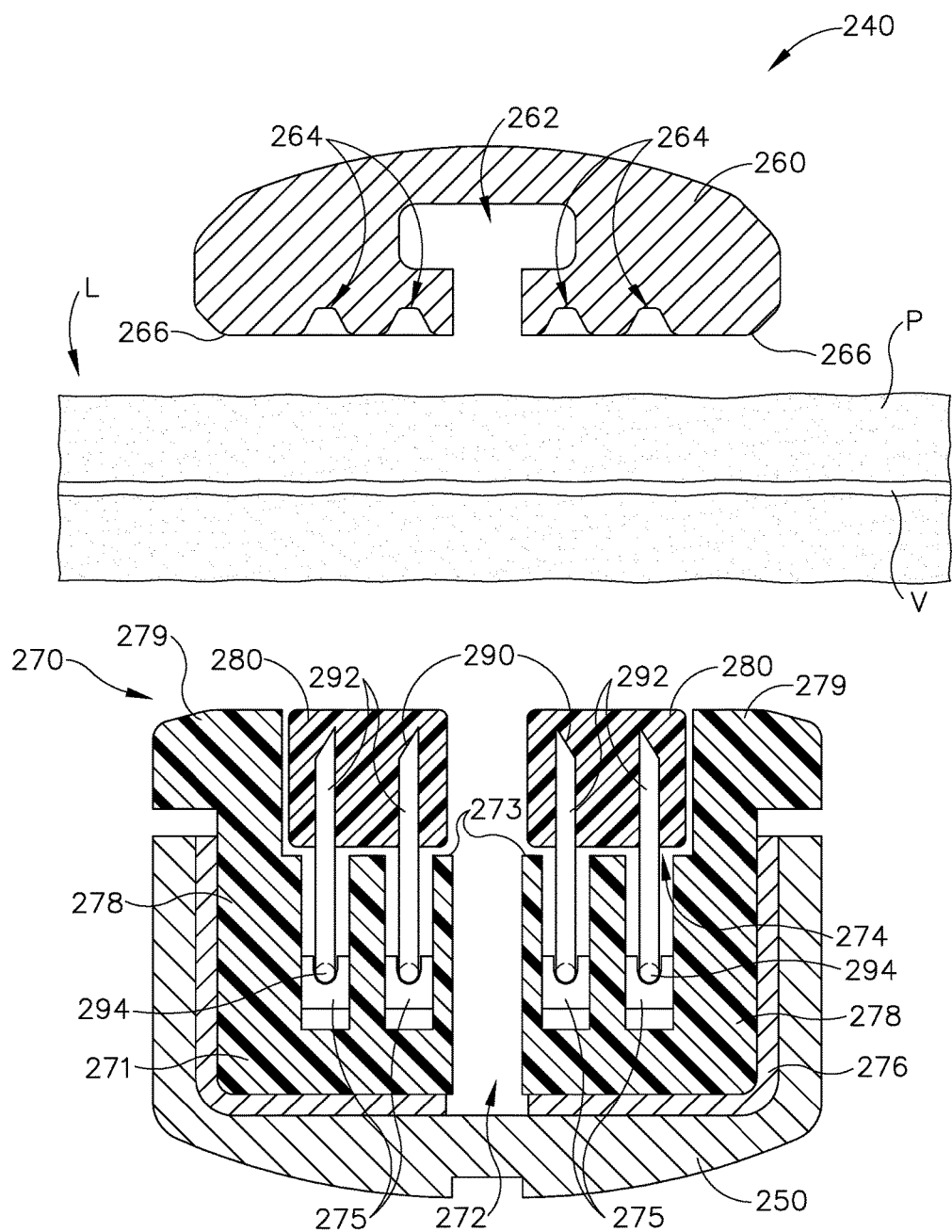
FIG. 9A depicts a front cross-sectional view of the end effector of FIG. 8, where the end effector is in an open position with a portion of liver between the anvil and the cartridge.
Figure 9B:
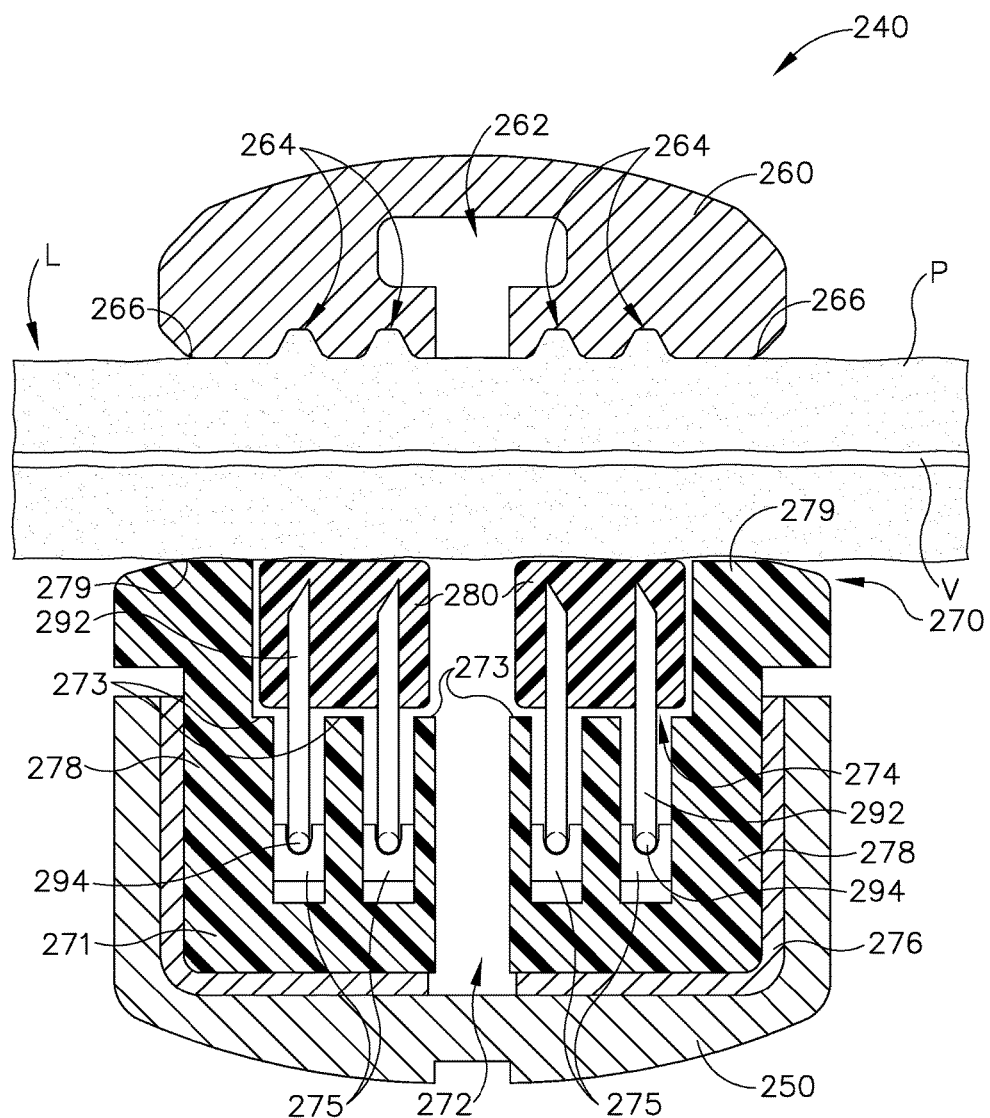
FIG. 9B depicts a front cross-sectional view of the end effector of FIG. 8, where the end effector is clamped against a portion of liver between the anvil and the cartridge.
Figure 9C:
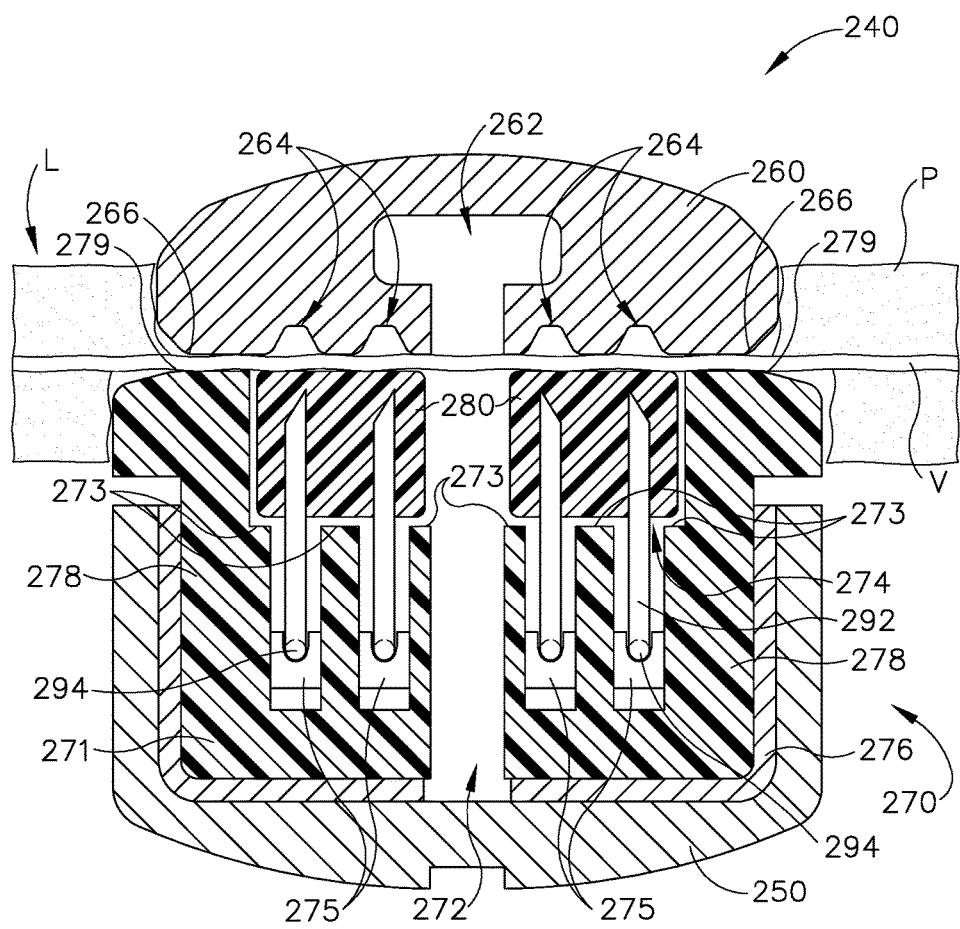
FIG. 9C depicts a front cross-sectional view of the end effector of FIG. 8, where the end effector is in a closed position after pinching through parenchyma tissue of the liver.

FIGS. 8-9C show an exemplary end effector (240) that may be incorporated into instrument (10). End effector (240) includes a lower jaw (250), an anvil (260), and a staple cartridge (270). It should be understood that while end effector (240) does not specifically show knife member (80) or wedge sled (78), end effector (240) may be configured to work with knife member (80) and wedge sled (78) of end effector (40) described above. Similar to anvil (60, 160) and lower jaw (50, 150) respectively, anvil (260) is pivotable toward and away from lower jaw (250) between an open position and a closed position.

Lower jaw (250) is substantially similar to lower jaw (250) described above. Therefore, lower jaw (250) is configured to receive staple cartridge (270). Staple cartridge (270) may be inserted into lower jaw (250), end effector (240) may be actuated, and then staple cartridge (270) may be removed and replaced with another staple cartridge (270). Lower jaw (250) thus releasably retains staple cartridge (270) in alignment with anvil (260) for activation of end effector (140). It should also be understood that some versions of staple cartridge (270) may be configured to be fully compatible with end effector (40) described above, such that cartridge (270) may fit in lower jaw (50) and be used with anvil (60).

Staple cartridge (270) of the present example comprises a cartridge body (271) and a tray (276) secured to the underside of cartridge body (271). An upper side of cartridge body (271) presents a deck (273) defining a plurality of staple pockets (274). Cartridge body (271) also includes a peripheral member (278) extending upwardly above and around the outer lateral perimeter of staple deck (273) and staple pockets (247). Peripheral member (278) terminates into a pinching surface (279). As will be described in greater detail below, peripheral member (278) and pinching surface (279) are configured to provide an opposing pinching force against soft tissue in response to anvil (260) pivoting from an open position to a closed position while soft tissue is positioned between anvil (260) and compressible buttress (280). In other words, peripheral member (278) and pinching surface (279) may prevent the free ends of staple legs (292) from penetrating the top surface of compressible buttress (280). In addition or in the alternative, peripheral member (278) may serve as a guard preventing the free ends of staple legs (292) from snagging on the soft tissue that is pinched by pinching surface (279).

A staple (290) is positioned within each staple pocket (274). Each staple (290) includes a crown (294) extending between a pair of legs (292). Legs (292) of staples (290) are dimensioned to extend from crown (294) within each corresponding staple pocket (274) and terminate above deck (273). Compressible buttress (280) is positioned on top of deck (273). The exposed free ends of legs (292) penetrate compressible buttress (280), thereby securing compressible buttress (280) to staples (290). Compressible buttress (280) may be made out of a resilient material such that if an object, such as a vein or bile duct, is pressed against compressible buttress (280) to compress the surface of buttress (280), compressible buttress (280) would apply a reactionary force against the object due to the resilient nature of compressible buttress (280). It should be understood that legs (292) of staple (290) do not receive such a reactionary force due to the fact the free ends of legs (292) penetrate the surface of compressible buttress (280) rather than compress the surface of buttress (280).

A staple driver (275) is also positioned in each staple pocket (274), underneath a corresponding crown (294) of staple (290), and above tray (276). Similar to staple drivers (75, 175) described above, staple drivers (275) are operable to translate upwardly in staple pockets (274) to thereby drive staples (290) upwardly through staple pockets (274) and into engagement with anvil (260). In particular, horizontal translation of wedge sled (78) leads to vertical translation of staple drivers (275), similar to how wedge sled (78) interacts with staple drivers (75) mentioned above.

Anvil (260) of the present example comprises a longitudinally extending channel (262), a plurality of staple forming pockets (264), and lateral edges (266). As will be described in greater detail below, lateral edges (266) and pinching surfaces (279) of peripheral member (278) may provide a pinching force against soft tissue, such as parenchyma, when anvil (260) pivots from an open position to a closed position and soft tissue is positioned between anvil (260) and compressible buttress (280).

Channel (262) is configured to align with channel (272) of staple cartridge (270) when anvil (260) is in a closed position. Aligned channels (262, 272) may receive knife member (80). Each staple forming pocket (264) is positioned to lie over a corresponding staple pocket (274) of staple cartridge (270) when anvil (260) is in a closed position. Staple forming pockets (264) are configured to deform the legs (292) of staples (290) when staples (290) are driven through tissue and into anvil (260). In particular, staple forming pockets (264) are configured to bend the legs (292) of staples (290) to secure the formed staples (290) in the tissue. Staples (290) and compressible buttress (280) are dimensioned such that as staples (290) are driven against anvil (260) to bend legs (292) of staples (290), crowns (294) and legs (292) of staples (290) are still associated with compressible buttress (280). Therefore, after staple cartridge (270) is actuated, compressible buttress (280) remains with the staple line formed by staples (290).

Knife member (80) may be positioned within channels (262, 272) of anvil (260) and staple cartridge (270). Additionally, distal longitudinal translation of knife member (80) may also drive wedge sled (78) in the distal longitudinal direction in order to drive staples (290) in the vertical direction towards anvil (260). Therefore, distally presented cutting edge (84) of knife member (80) may sever tissue located within channels (262, 272) while wedge sledge (78) drives staples (290) against anvil (260) so that staples (290) are driven through tissue adjacent to channels (262, 272). While end effector (240) of the present example has two strips of buttress (280) positioned on each side of channel (272), some other versions may have just a single strip of buttress (280) spanning across channel (272), extending across the full width of deck (273). In such versions, cutting edge (84) may also cut through buttress (280) as cutting edge (84) cuts through tissue.

As seen in FIGS. 8-9C, peripheral member (278) extends above both staple deck (273) and the top surface of compressible buttress (280) such that pinching surface (279) is above the free end of staple legs (292). FIGS. 9A-9C show a sequence where end effector (240) transitions from an open configuration to a closed configuration while grasping a liver (L), thereby pinching parenchyma (P). In particular, FIG. 9A shows parenchyma (P) and vein (V) positioned between anvil (260) and staple cartridge (270), with anvil (260) in the open position. Next, trigger (24) is pivoted toward pistol grip (22) to drive closure tube (32) and closure ring (36) distally. This drives anvil (260) toward the closed position and against the outside of parenchyma (P) defining the outer surface of liver (L) as shown in FIG. 9B. At this point, the bottom surface of anvil (260) and the pinching surface (279) of peripheral member (278) are in contact with the parenchyma (P). The operator may further pivot anvil (260) toward the closed position as shown in FIG. 9C.

When anvil (260) is pivoting from the position shown in FIG. 9B to the position shown in FIG. 9C, pinching surface (279) and lateral edge (266) cooperate to impart a pinching force on parenchyma (P), thereby cutting through a section of liver (L). As noted above, peripheral member (278) serves as a guard to prevent frees end of staple legs (292) from penetrating the top surface of compressible member (280) during the closure of anvil during the transition between the states shown in FIGS. 9B-9C, such that peripheral member (278) prevents free ends of staple legs (292) from snagging on the parenchyma (P). As also seen in FIG. 9C, vein (V) is still located between anvil (260) and cartridge (270). The operator may then actuate end effector (240) to sever a portion of vein (V) between channels (262, 272) and staple the severed ends of vein (V), similar to the sequence shown in FIGS. 7B-7C.

C. Exemplary End Effector with Peripheral Pinching Cartridge and Compliant Pinching Surface As described above, an operator may close anvil (260) toward staple cartridge (270) in order to provide a pinching force against soft tissue located between anvil (260) and staple cartridge (270). In some instances, a vein (V) may be located within the soft tissue being sheared without knowledge to the operator. If the operator is unaware of the presence of vein (V) between anvil (260) and staple cartridge (270), an operator may pivot anvil (260) too close to staple cartridge (270) and accidentally shear a portion of vein (V) located between lateral edge (266) and pinching surface (279), leading to a damaged portion of vein (V) located exterior to the potentially severed and stapled open ends of vein (V). Therefore, it may be beneficial to provide an end effector that is capable of preventing or indicating to an operator the presence of a vein (V), bile duct (B), or any other tubular anatomy located between anvil (260) and staple cartridge (270). In addition or in the alternative, it may be beneficial to provide an end effector that has a guard feature similar to peripheral member (278) that prevents free ends of staple legs (292) from snagging on soft tissue (e.g., liver parenchyma (P)); but with a modification to prevent the guard feature from undesirably shearing anatomical lumens (e.g., veins (V) or bile ducts (B)) that are located within the soft tissue.

Figure 10:
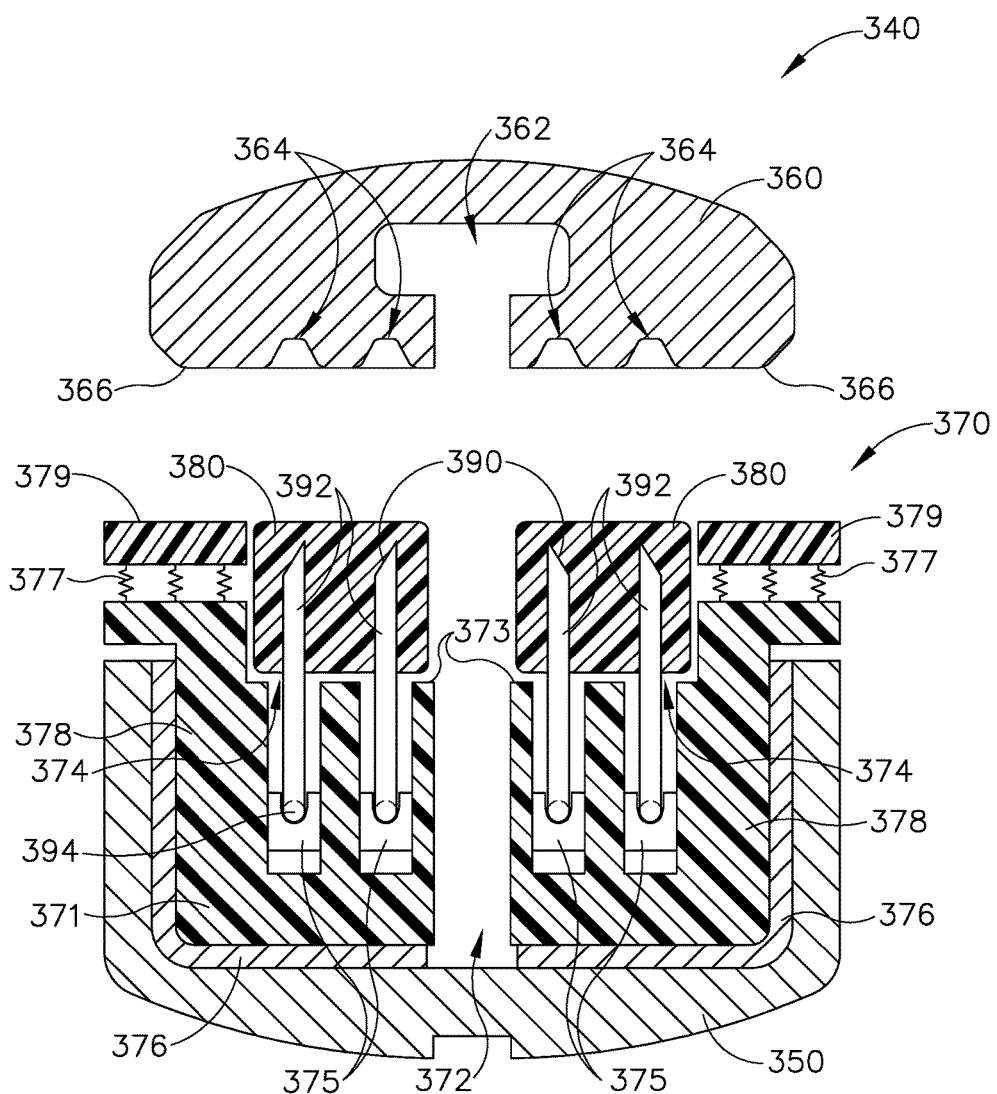
FIG. 10 depicts a front cross-sectional view of another exemplary end effector that may be readily incorporated into the instrument of FIG. 1.

FIG. 10 shows an end effector (340) that may be readily incorporated into instrument (10). End effector (340) includes a lower jaw (350), an anvil (360), and a staple cartridge (370), which are substantially similar to end lower jaw (250), anvil (260), and staple cartridge (270) mentioned above, with differences described below. It should therefore be understood that lower jaw (350) may releasably hold staple cartridge (370). It should also be understood that some versions of staple cartridge (370) may be configured to be fully compatible with end effector (40) described above, such that cartridge (370) may fit in lower jaw (50) and be used with anvil (60). Anvil (360) of the present example includes lateral edges (366) that are substantially similar to lateral edges (266) described above. Anvil (360) defines a longitudinally extending channel (362) and staple forming pockets (364) that are substantially similar to longitudinally extending channel (262) and staple forming pockets (262) described above.

Staple cartridge (370) includes a cartridge body (371), a deck (373), staple drivers (375), a tray (376), a peripheral member (378) and pinching surface (379), substantially similar to cartridge body (271), deck (273), staple drivers (275), tray (276), peripheral member (278), and pinching surface (279) mentioned above with differences described below. It should therefore be understood that deck (373) defines a plurality of staple pockets (374) and body (371) defines a longitudinally extending channel (372). Staples (390) each have a crown (394) that extends between corresponding legs (392), positioned above respective staple drivers (375). A compressible buttress (380) is located on top of deck (373), with free ends of legs (392) of staples (390) penetrating compressible buttress (380) to secure buttress (380) to deck (373). Compressible buttress (380) is substantially similar to compressible buttress (280) described above.

Unlike pinching surface (279) described above, pinching surface (379) of the present example is connected to peripheral member (378) with a spring connection (377). By way of example only, spring connection (377) may comprise a set of coil springs, a set of leaf springs, and/or any other suitable resilient component(s). In the present example, spring connection (377) has a spring constant such that pinching surface (379) does not move relative to peripheral member (378) while pinching surface (379) and lateral edge (366) cooperate to dissect parenchyma (P) or other soft tissue. In other words, spring connection (377) has sufficient stiffness such that spring connection (377) will not deform as pinching surface (379) and lateral edge (366) cooperate to dissect parenchyma (P) or other soft tissue. However, spring connection (377) has a spring constant that allows pinching surface (379) to move toward peripheral member (378) when pinching surface (379) and lateral edge (366) are pressed against an anatomical lumen such as a vein (V) or bile duct (B). In other words, spring connection (377) has sufficient compliance such that spring connection (377) will deform as pinching surface (379) and lateral edge (366) compress against an anatomical lumen such as a vein (V) or bile duct (B) (since the vein (V) or bile duct (B) may have stronger structural integrity than the parenchyma (P)). It should therefore be understood that movement of pinching surface (379) toward peripheral member (378) during potential pinching of anatomical lumens may help prevent end effector (340) from prematurely transecting the anatomical lumens.

Figure 11:
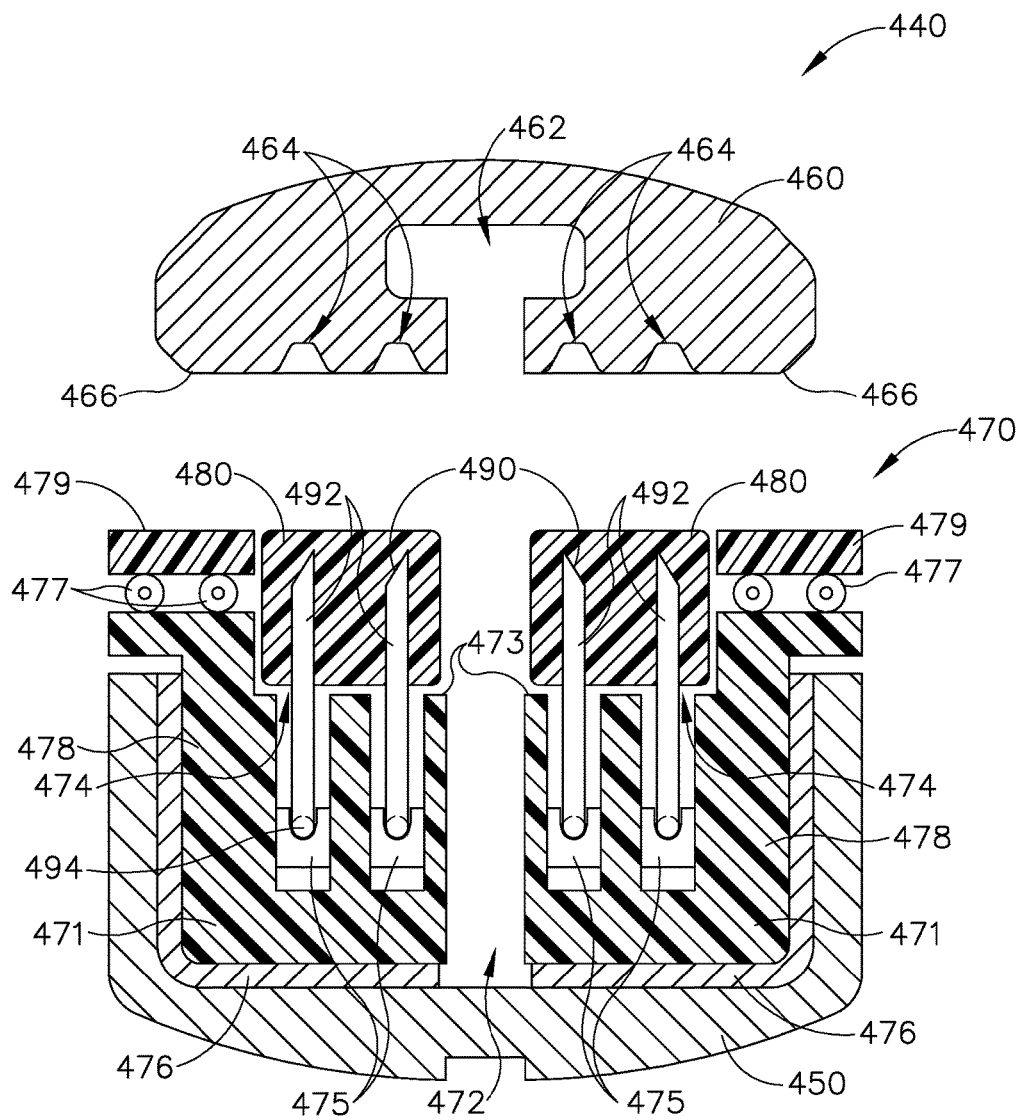
FIG. 11 depicts a front cross-sectional view of another exemplary end effector that may be readily incorporated into the instrument of FIG. 1.

While a spring connection (377) is used in the above-described example, it should be understood that any other suitable structure having a sufficient spring constant may be used as would be apparent to one having ordinary skill in the art in view of the teachings herein. For instance, FIGS. 11-12C show an exemplary end effector (440) that may be readily incorporated into instrument (10). End effector (440) of this example includes a lower jaw (450), an anvil (460), and a staple cartridge (470), which are substantially similar to end lower jaw (350), anvil (360), and staple cartridge (370) mentioned above, with differences described below. It should therefore be understood that lower jaw (450) may releasably hold staple cartridge (470). It should also be understood that some versions of staple cartridge (470) may be configured to be fully compatible with end effector (40) described above, such that cartridge (470) may fit in lower jaw (50) and be used with anvil (60). Anvil (460) of the present example includes lateral edges (466) that are substantially similar to lateral edges (366) described above. Anvil (460) defines a longitudinally extending channel (462) and staple forming pockets (464) that are substantially similar to longitudinally extending channel (362) and staple forming pockets (362) described above.

Staple cartridge (470) includes a cartridge body (471), a deck (473), staple drivers (475), a tray (476), a peripheral member (478), and pinching surface (479), substantially similar to cartridge body (371), deck (373), staple drivers (375), tray (376), peripheral member (378), and pinching surface (379) described above with differences described below. It should therefore be understood that deck (473) defines a plurality of staple pockets (474) and body (471) defines a longitudinally extending channel (472). Staples (490) each have a crown (494) that extends between corresponding legs (492), positioned above respective staple drivers (475). A compressible buttress (480) is located on top of deck (473), with free ends of legs (492) of staples (490) penetrating compressible buttress (480) to secure buttress (480) to deck (473). Compressible buttress (480) is substantially similar to compressible buttress (380) described above.

Pinching surface (479) is connected to peripheral member (478) with sets of resilient filaments (477). Resilient filaments (477) have a spring constant such that pinching surface (479) does not move relative to peripheral member (478) while pinching surface (479) and lateral edge (466) cooperate to dissect parenchyma (P) or other soft tissue. In other words, resilient filaments (477) have sufficient stiffness such that resilient filaments (477) will not deform as pinching surface (479) and lateral edge (466) cooperate to dissect parenchyma (P) or other soft tissue. However, resilient filaments (477) have a spring constant that allows pinching surface (479) to move toward peripheral member (478) when are pressed against an anatomical lumen such as a vein (V) or bile duct (B). In other words, resilient filaments (477) have sufficient compliance such that resilient filaments (477) will deform as pinching surface (479) and lateral edge (466) compress against an anatomical lumen such as a vein (V) or bile duct (B) (since the vein (V) or bile duct (B) may have stronger structural integrity than the parenchyma (P)). It should therefore be understood that movement of pinching surface (479) toward peripheral member (478) during potential pinching of anatomical lumens may help prevent end effector (440) from prematurely transecting the anatomical lumens.

Figure 12A:
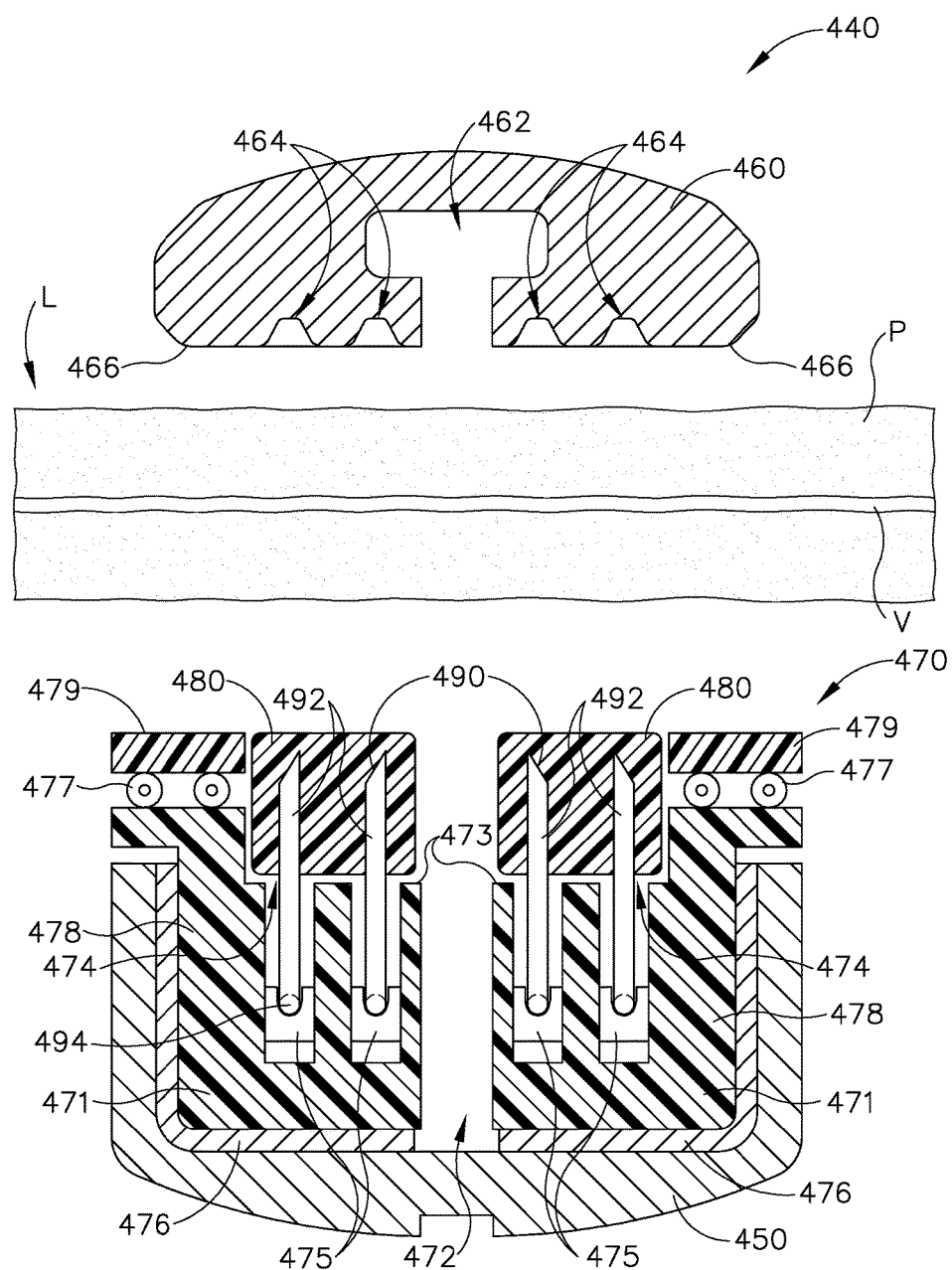
FIG. 12A depicts a front cross-sectional view of the end effector of FIG. 11, where the end effector is in an open position with a portion of liver between the anvil and the cartridge.
Figure 12B:
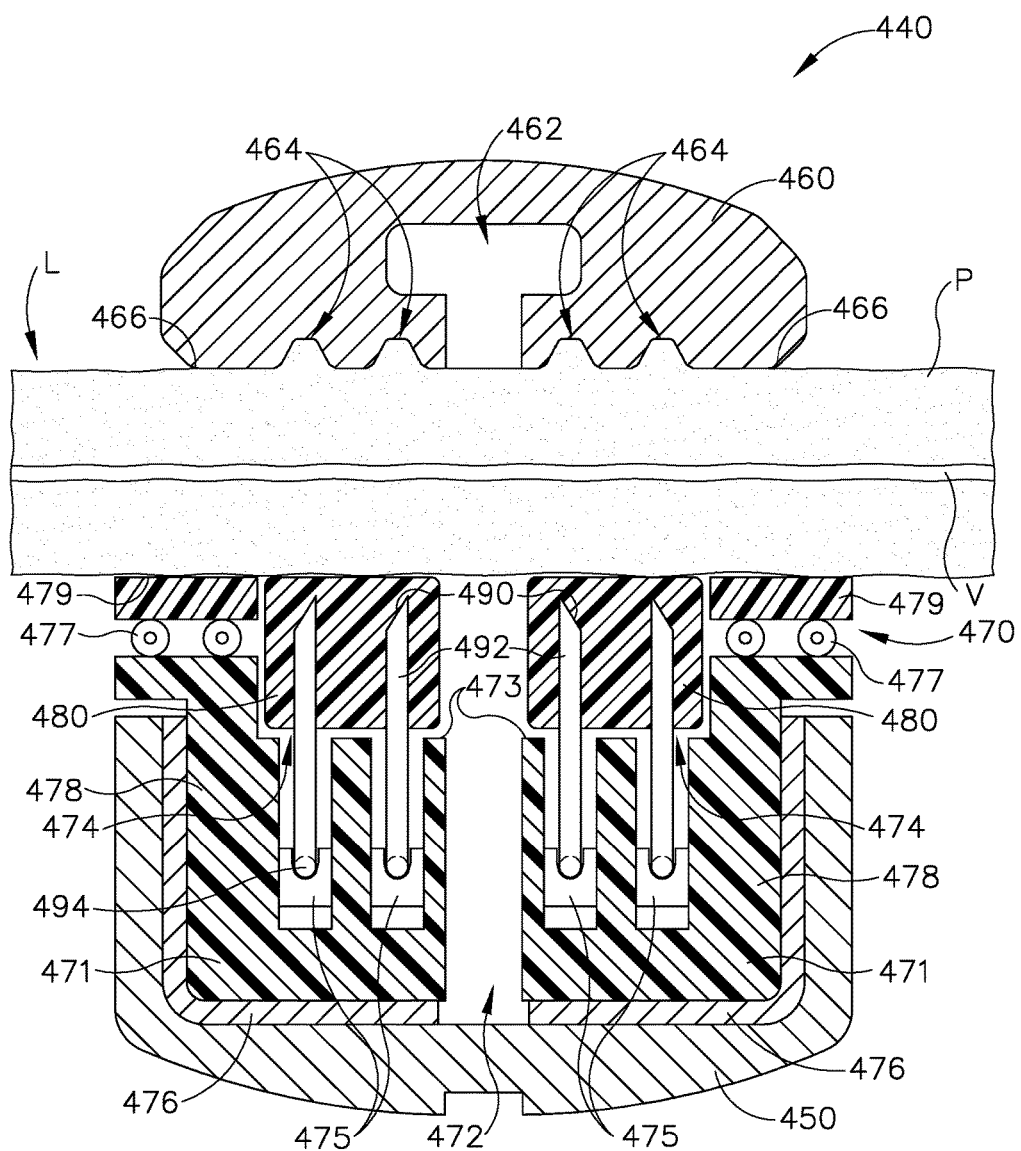
FIG. 12B depicts a front cross-sectional view of the end effector of FIG. 11, where the end effector is clamped against a portion of liver between the anvil and the cartridge.
Figure 12C:
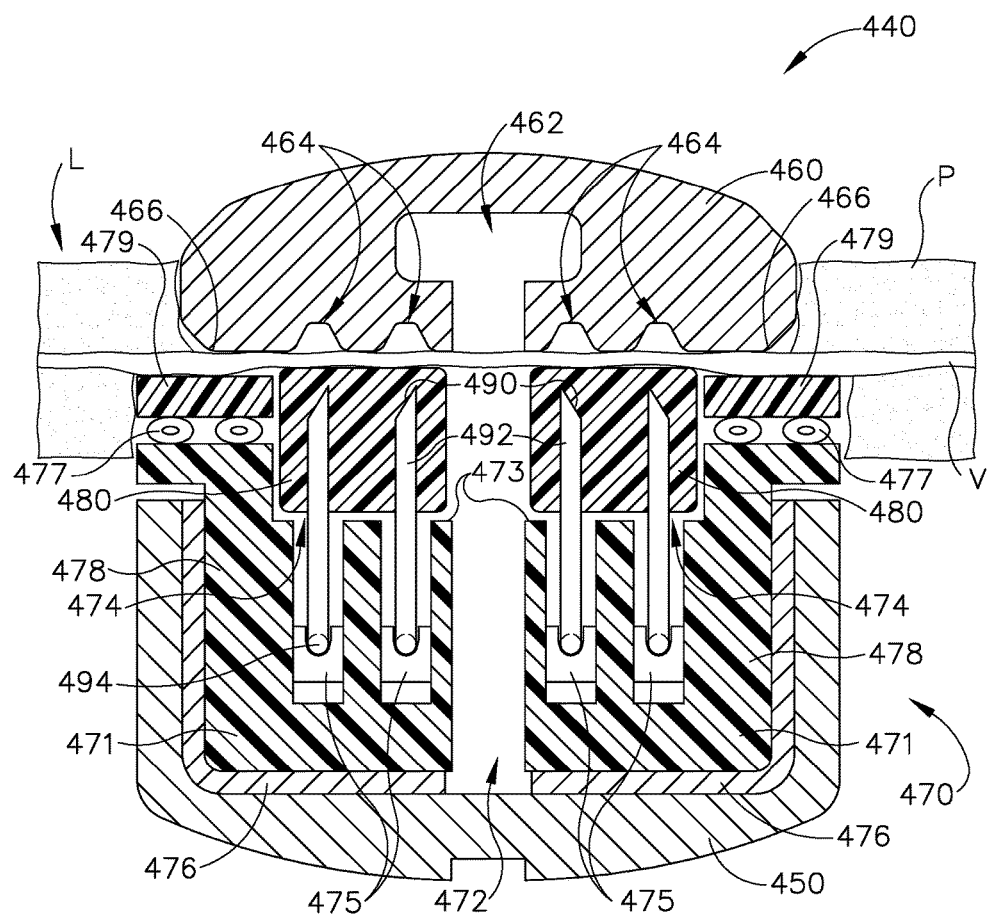
FIG. 12C depicts a front cross-sectional view of the end effector of FIG. 11, where the end effector is in a closed position after pinching through parenchyma tissue of the liver.

FIGS. 12A-12C show a sequence where end effector (440) transitions from an open configuration to a closed configuration while grasping a liver (L), thereby pinching parenchyma (P). In particular, FIG. 12A shows parenchyma (P) and vein (V) positioned between anvil (460) and staple cartridge (470), with anvil (460) in the open position. Next, trigger (24) is pivoted toward pistol grip (22) to drive closure tube (32) and closure ring (36) distally. This drives anvil (460) toward the closed position and against the outside of parenchyma (P) defining the outer surface of liver (L), as shown in FIG. 12B. At this point, the bottom surface of anvil (460) and the pinching surface (479) of peripheral member (478) are in contact with the outside of parenchyma (P).

The operator may further pivot anvil (460) toward the closed position as shown in FIG. 12C. When anvil (460) is pivoting from the position shown in FIG. 12B to the position shown in FIG. 12C, pinching surface (479) and lateral edge (466) impart a pinching force on parenchyma (P), thereby cutting through a section of liver (L). It should be understood that the spring constant of resilient filament (477) is great enough that the force required to dissect parenchyma (P) does not cause pinching surface (479) to compress resilient filament (477) during the transition from the state shown in FIG. 12B to the state shown in FIG. 12C. As also seen in FIG. 12C, vein (V) is still located between anvil (460) and cartridge (470) and has not been dissected. If the operator continues to pivot anvil (460) beyond the point where pinching surface (479) and lateral edge (466) have fully dissected the parenchyma (P), resilient filament (477) will compress toward peripheral member (478), such that resilient filament (477) absorbs the additional compression force to prevent damage to vein (V). Some versions of end effector (440) are configured such that anvil (460) will pivot no further toward cartridge (470) after resilient filaments (477) have been compressed, such that end effector (440) will not dissect vein (V) after filaments (477) have been compressed.

It should be understood that pinching surface (479) of peripheral member (478) may also help prevent the free ends of staple legs (492) from penetrating the top surface of compressible member (480) and snagging on the parenchyma (P) during the closure of anvil (460) as shown in FIGS. 12B-12C. After anvil (460) has been closed to the point shown in FIG. 12C, the operator may then actuate end effector (440) to sever a portion of vein (V) in between channels (462, 472) and staple the severed ends of the vein (V), similar to the sequence shown in FIGS. 7B-7C.

Figure 13:
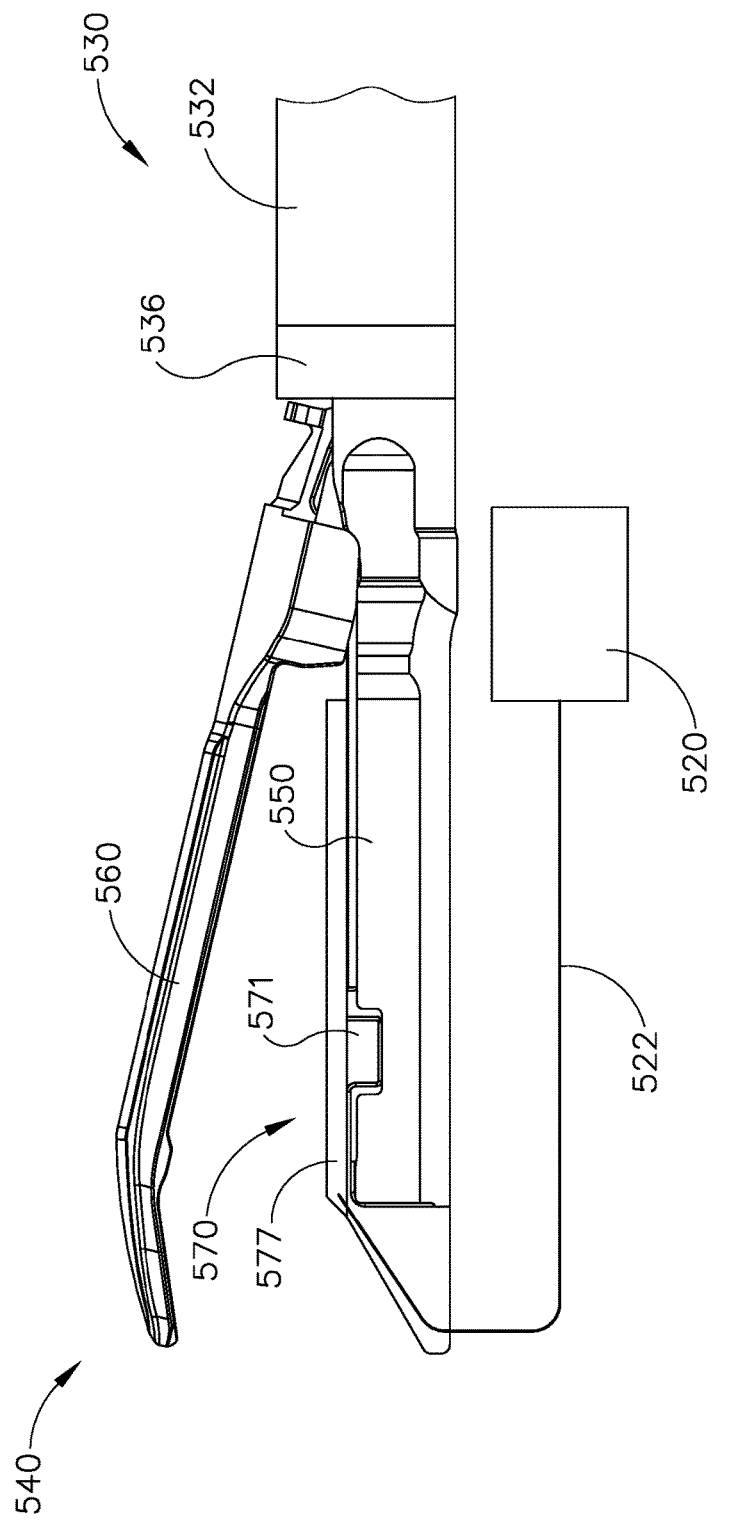
FIG. 13 depicts a side elevational view of an exemplary end effector and shaft assembly that may be readily incorporated into the instrument of FIG. 1.

In some instances, it may be desirable to inform an operator that a vein (V) or bile duct (B) is present between anvil (460) and staple cartridge (470). This may help prevent an operator from unnecessarily pinching an anatomical lumen located between lateral edge (466) and pinching surface (479). To that end, FIGS. 13-14C show another exemplary end effector (540) and shaft assembly (530) that may be readily incorporated into instrument (10). As will be described in greater detail below, end effector (540) is configured to inform an operator that further pivoting of anvil (560) toward staple cartridge (570) may potentially shear tubular anatomy such as a vein (V) or bile duct (B) between a pinching surface (579) of a staple cartridge (570) and lateral edges (566) of an anvil (560).

Shaft assembly (530) of the present example includes an outer closure tube (532) and a closure ring (536), which are substantially similar to outer closure tube (32) and closure ring (36) described above. End effector (540) includes a lower jaw (550), an anvil (560), and a staple cartridge (570), which are substantially similar to end lower jaw (250), anvil (260), and staple cartridge (270) mentioned above, with differences described below. It should therefore be understood that lower jaw (550) may releasably hold staple cartridge (570). Anvil (560) includes lateral edges (566) substantially similar to lateral edges (266) described above. Anvil defines a longitudinally extending channel (562) and staple forming pockets (564), substantially similar to longitudinally extending channel (262) and staple forming pockets (262) described above.

Staple cartridge (570) includes a cartridge body (571), a deck (573), staple drivers (575), a tray (576), a peripheral member (578), and a pinching surface (579), which are substantially similar to cartridge body (271), deck (273), staple drivers (275), tray (276), peripheral member (278), and pinching surface (279) described above with differences described below. It should therefore be understood that deck (573) defines a plurality of staple pockets (574) and body (571) defines a longitudinally extending channel (572). Staples (590) each have a crown (594) extending between corresponding legs (592) and are positioned above respective staple drivers (575). A compressible buttress (580) is located on top of deck (573), with legs (592) of staples (590) penetrating compressible buttress (580) to secure buttress (580) to deck (573). Compressible buttress (580) is substantially similar to compressible buttress (280) described above.

Figure 14A:
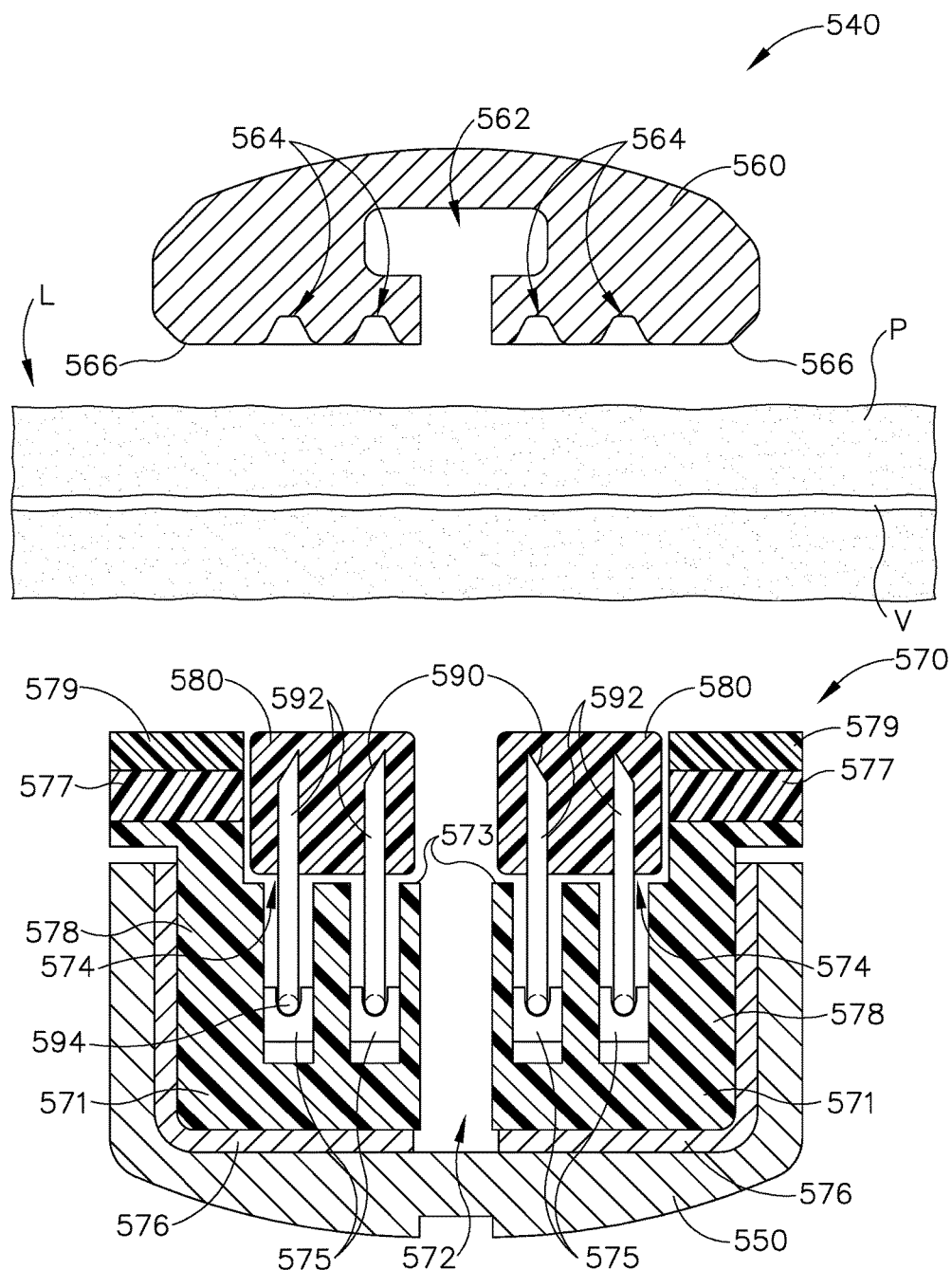
FIG. 14A depicts a front cross-sectional view of the end effector of FIG. 13, where the end effector is in an open position with a portion of liver between the anvil and the cartridge.
Figure 14B:
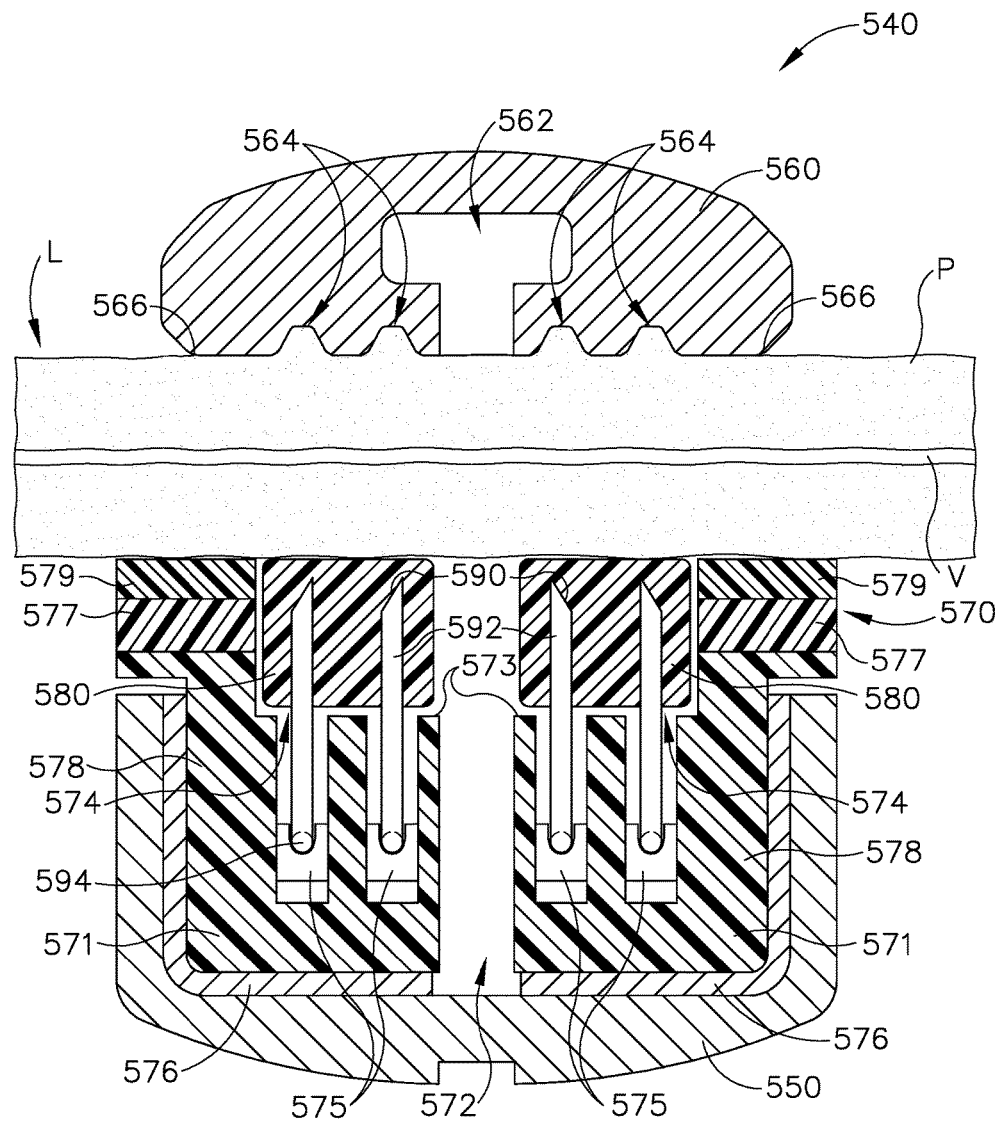
FIG. 14B depicts a front cross-sectional view of the end effector of FIG. 13, where the end effector is clamped against a portion of liver between the anvil and the cartridge.
Figure 14C:
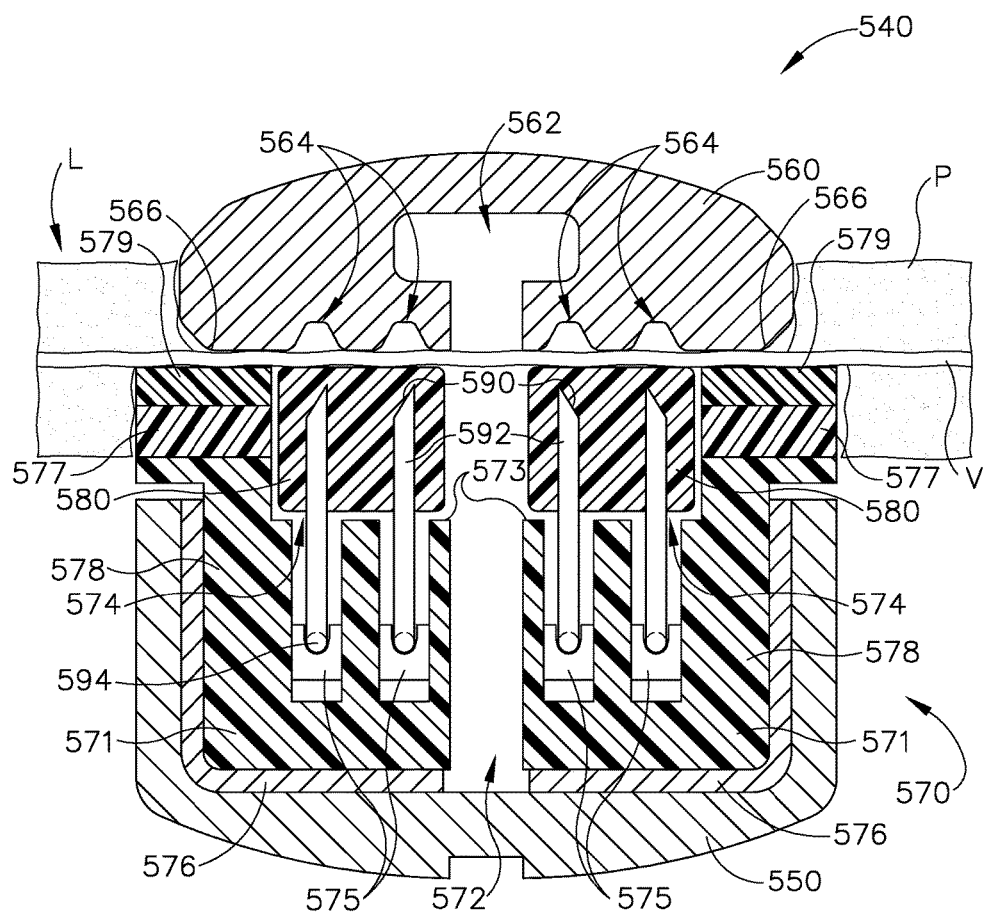
FIG. 14C depicts a front cross-sectional view of the end effector of FIG. 13, where the end effector is in a closed position after pinching through parenchyma tissue of the liver.

As can be seen in FIGS. 14A-14C, pinching surface (579) is connected to peripheral member (578) via a force sensor (577). Force sensor (577) is configured to measure the downward force applied to pinching surface (579) in response to tissue being sheared or compressed between lateral edges (566) of anvil (560) and pinching surface (579). By way of example only, force sensor (577) may comprise a conventional strain gauge and/or any other suitable kind of force sensor (577) as will be apparent to those of ordinary skill in the art in view of the teachings herein. It should also be understood that an array of force sensors (577) may be used. For instance, several force sensors (577) may be positioned between each pinching surface (579) and peripheral member (578), with the force sensors being longitudinally spaced apart from each other by any suitable distance. Other suitable components and arrangements that may be used to provide force sensors (577) will be apparent to those of ordinary skill in the art in view of the teachings herein.

As can be seen in FIG. 13, force sensor (577) is in communication with an indicator device (520) via a wire (522). While force sensor (577) is in communication with indicator device (520) via a wire (522) in the present example, it should be understood that any other suitable connection may be used as would be apparent to one having ordinary skill in the art in view of the teachings herein. For example, end effector (540) may include pins while shaft assembly (530) may include electrical traces extending from shaft assembly (530) to body (22). The electrical traces and pins may allow for communication between force sensor (577) and indicator device (520). Additionally, while indicator device (520) is located exterior to the rest of instrument (10) in this particular example, it should be understood that indicator device (520) may be located at any suitable location relative to the rest of instrument (10) as would be apparent to one having ordinary skill in the art in view of the teachings herein. For example, indicator device (520) may be located on the exterior or interior of body (22).

As will be described in greater detail below, once force sensor (577) detects a force above what is required to shear soft tissue (e.g., liver parenchyma (P)), force sensor (577) may activate indicator device (520), which may signal to an operator that potential tubular anatomy (e.g., vein (V) or bile duct (B)) is located between anvil (560) and staple cartridge (570). Indicator device (520) may activate an auditory signal, a visual signal, a tactile signal, and/or any other form of feedback to inform the operator that tubular anatomy (e.g., vein (V) or bile duct (B)) is located between anvil (560) and staple cartridge (570). Various suitable forms of user feedback that may be provided will be apparent to those having ordinary skill in the art in view of the teachings herein.

FIGS. 14A-14C show a sequence where end effector (540) transitions from an open configuration to a closed configuration while grasping a liver (L), thereby pinching parenchyma (P). In particular, FIG. 15A shows parenchyma (P) and vein (V) positioned between anvil (560) and staple cartridge (570), with anvil (560) in the open position. Next, trigger (24) is pivoted toward pistol grip (22) to drive closure tube (532) and closure ring (536) distally. This drives anvil (560) toward the closed position and against the outside of parenchyma (P) defining the outer surface of liver (L) as shown in FIG. 14B. At this point, the bottom surface of anvil (560) and the pinching surface (579) of peripheral member (578) are in contact with the outside a parenchyma (P).

The operator may further pivot anvil (560) toward the closed position as shown in FIG. 14C. When anvil (560) is pivoting from the position shown in FIG. 14B to the position shown in FIG. 14C, pinching surface (579) and lateral edge (566) impart a pinching force on parenchyma (P), thereby cutting through a section of liver (L). Force sensor (577) reads the corresponding force on pinching surface (579). It should be understood that the force read by force sensor (577) is small enough that the force required to shear parenchyma (P) does not cause force sensor (577) to activate indicator device (520). As also seen in FIG. 14C, vein (V) is located between anvil (560) and cartridge (570). If the operator continues to pivot anvil (560) too far, such that lateral edges (566) and pinching surface (579) may potentially shear and damage vein (V), force sensor (577) may trigger activation of indicator device (520), thereby signaling to an operator that further closure of anvil (560) toward staple cartridge (570) may damage vein (V). It should be understood that pinching surface (579) of peripheral member (578) may also help prevent the free ends of staple legs (592) from penetrating the top surface of compressible member (580) and snagging on the parenchyma (P) during the closure of anvil (560) as shown in FIGS. 14B-14C.

With knowledge that vein (V) is captured between anvil (560) and staple cartridge (570), the operator may then stop pivoting of anvil (560) toward staple cartridge (570); and actuate end effector (540) to sever a portion of vein (V) in between channels (562, 572) and staple the severed ends, similar to the sequence shown in FIGS. 7B-7C.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus, the apparatus comprising: (a) a body assembly; (b) a shaft extending distally from the body assembly; (c) an end effector attached to the shaft, wherein the end effector comprises: (i) a jaw, and(ii) an anvil pivotable from an open position to a closed position relative to the jaw; and (d) a cartridge, wherein the cartridge comprises: (i) a deck comprising an upper surface facing toward the anvil in the closed position, wherein the deck defines a plurality of openings, (ii) a plurality of staples located within the plurality of openings, wherein each staple in the plurality of staples comprises a pair of legs extending above the upper surface of the deck, (iii) a compressible buttress located on the upper surface of the deck, wherein portions of the legs of the staples are disposed the compressible buttress, (iv) a peripheral member extending above the upper surface of the deck, laterally adjacent to the compressible buttress, and (v) a pinching surface associated with the peripheral member, wherein the pinching surface is located at a height extending above a height of the legs of the plurality of staples.

EXAMPLE 2

The apparatus of Example 1, wherein the pinching surface is located at a height extending above a height of the legs of the compressible buttress.

EXAMPLE 3

The apparatus of any one or more of Examples 1 through 2, wherein the peripheral member is unitarily connected to the pinching surface.

EXAMPLE 4

The apparatus of any one or more of Examples 1 through 3, wherein the peripheral member is connected to the pinching surface by a resilient connection.

EXAMPLE 5

The apparatus of Example 4, wherein the pinching surface is configured to deflect downwardly toward the peripheral member in response to an external force.

EXAMPLE 6

The apparatus of Example 5, wherein the pinching surface is configured to shear parenchyma tissue capture between the anvil and the cartridge when the anvil pivots toward the closed position, wherein the pinching surface is configured to shear parenchyma without deflecting downwardly toward the peripheral member.

EXAMPLE 7

The apparatus of Example 6, wherein the resilient connection comprises a resilient filament.

EXAMPLE 8

The apparatus of any one or more of Examples 6 through 7, wherein the resilient connection comprises a spring.

EXAMPLE 9

The apparatus of any one or more of Examples 1 through 8, wherein the peripheral member is connected to the pinching surface by a force sensor.

EXAMPLE 10

The apparatus of Example 9, wherein the force sensor is configured to measure an external force applied to the pinching surface.

EXAMPLE 11

The apparatus of Example 10, wherein the force sensor is in electrical communication with an indicator device.

EXAMPLE 12

The apparatus of Example 11, wherein the indicator device is configured to activate in response to the force sensor measuring an external force above a predetermined threshold value.

EXAMPLE 13

The apparatus of any one or more of Examples 1 through 12, wherein the anvil comprises a lateral edge, wherein the lateral edge and the pinching surface are configured to shear tissue located between the anvil and the cartridge when the anvil pivots from the open position to the closed position.

EXAMPLE 14

The apparatus of Example 13, wherein the anvil defines a first longitudinal channel, wherein the cartridge defines a second longitudinal channel, wherein the apparatus further comprises a knife member configured to translate within the first longitudinal channel and the second longitudinal channel when the anvil is in the closed position.

EXAMPLE 15

The apparatus of Example 14, wherein the apparatus further comprises a wedge sled, wherein the wedge sled is associated with the knife member, wherein the wedge sled is configured to drive the plurality of staples toward the anvil when the knife member translates within the first longitudinal channel and the second longitudinal channel.

EXAMPLE 16

The apparatus of Example 15, wherein the anvil further comprises a plurality of staple forming pockets, wherein the staple forming pockets are configured to align with the plurality of openings of the deck when the anvil is in the closed position.

EXAMPLE 17

An apparatus, the apparatus comprising: (a) a body assembly; (b) a shaft extending distally from the body assembly; (c) an end effector attached to the shaft, wherein the end effector comprises: (i) a jaw, and (ii) an anvil pivotable from an open position to a closed position relative to the jaw; and (d) a cartridge configured to align with the anvil while the anvil is in the closed position, wherein the cartridge comprises: (i) a deck defining a plurality of openings, (ii) a plurality of staples positioned within the plurality of openings, wherein each staple in the plurality of staples comprises a pair of legs extending above the deck, (iii) a compressible buttress attached to the legs of the staples, wherein the buttress is located on the upper surface of the deck, and (iv) a peripheral member defining a pinching surface, wherein the pinching surface is configured to face the anvil while the anvil is in the closed position, wherein the pinching surface is located at a height positioned above a height of the legs of the plurality of staples.

EXAMPLE 18

The apparatus of Example 17, wherein the peripheral member further comprises a resilient member attached to a bottom of the pinching surface.

EXAMPLE 19

The apparatus of any one or more of Examples 17 through 18, wherein the peripheral member further comprises a force sensor attached to the bottom of the pinching surface.

EXAMPLE 20

An apparatus, the apparatus comprising: (a) a body assembly; (b) a shaft extending distally from the body assembly; (c) an end effector attached to the shaft, wherein the end effector comprises: (i) a jaw, and (ii) an anvil pivotable from an open position to a closed position relative to the jaw; and (d) a cartridge removably attached to the jaw, wherein the cartridge comprises: (i) a deck comprising an upper surface configured to face toward the anvil in the closed position, wherein the deck defines a plurality of openings, (ii) a plurality of staples located within the plurality of openings, wherein each staple in the plurality of staples comprises a pair of legs extending above the upper surface of the deck, (iii) a compressible buttress located on the upper surface of the deck, wherein portions of the legs of the staples are positioned in compressible buttress, and (v) a pinching surface located adjacent to the compressible buttress, wherein the pinching surface extends to a height located above a height of the legs of the staples.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,605,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, the apparatus comprising:
   (a) a body assembly;
   (b) a shaft extending distally from the body assembly;
   (c) an end effector attached to the shaft, wherein the end effector comprises:
      (i) a jaw, and
      (ii) an anvil pivotable from an open position to a closed position relative to the jaw, wherein the anvil comprises a lateral edge located at a first lateral position; and
   (d) a cartridge, wherein the cartridge comprises:
      (i) a deck comprising an upper surface facing toward the anvil in the closed position, wherein the deck defines a plurality of openings,
      (ii) a plurality of staples located within the plurality of openings, wherein each staple in the plurality of staples comprises a pair of legs extending above the upper surface of the deck,
      (iii) a compressible buttress located on the upper surface of the deck, wherein portions of the legs of the staples are disposed in the compressible buttress,
      (iv) a peripheral member extending above the upper surface of the deck, laterally adjacent to the compressible buttress, and
      (v) a pinching surface associated with the peripheral member, wherein the pinching surface is located at a height extending above a height of the legs of the plurality of staples, wherein the first lateral position of the lateral edge of the anvil is laterally aligned with the pinching surface such that the lateral edge and the pinching surface share a common lateral position.

2. The apparatus of claim 1, wherein the peripheral member is unitarily connected to the pinching surface.

3. The apparatus of claim 1, wherein the lateral edge and the pinching surface are configured to shear tissue located between the anvil and the cartridge when the anvil pivots from the open position to the closed position.

4. The apparatus of claim 3, wherein the anvil defines a first longitudinal channel, wherein the cartridge defines a second longitudinal channel, wherein the apparatus further comprises a knife member configured to translate within the first longitudinal channel and the second longitudinal channel when the anvil is in the closed position.

5. The apparatus of claim 4, wherein the apparatus further comprises a wedge sled, wherein the wedge sled is associated with the knife member, wherein the wedge sled is configured to drive the plurality of staples toward the anvil when the knife member translates within the first longitudinal channel and the second longitudinal channel.

6. The apparatus of claim 5, wherein the anvil further comprises a plurality of staple forming pockets, wherein the staple forming pockets are configured to align with the plurality of openings of the deck when the anvil is in the closed position.

7. An apparatus, the apparatus comprising:
(a) a body assembly;
(b) a shaft extending distally from the body assembly;
(c) an end effector attached to the shaft, wherein the end effector comprises:
   (i) a jaw, and
   (ii) an anvil pivotable from an open position to a closed position relative to the jaw, wherein the anvil comprises a lateral edge located at a first lateral position; and
(d) a cartridge configured to align with the anvil while the anvil is in the closed position, wherein the cartridge comprises:
   (i) a deck defining a plurality of openings,
   (ii) a plurality of staples positioned within the plurality of openings, wherein each staple in the plurality of staples comprises a pair of legs extending above the deck,
   (iii) a compressible buttress attached to the legs of the staples, wherein the compressible buttress is located on the upper surface of the deck, wherein the compressible buttress comprises an upper surface extending across a lateral range of positions, wherein the lateral edge is configured to be laterally offset from the upper surface of the compressible buttress when the anvil is in the closed position such that the first lateral position of the lateral edge is located outside the lateral range of positions of the upper surface of the compressible buttress, and
   (iv) a peripheral member defining a pinching surface, wherein the pinching surface is configured to face the anvil while the anvil is in the closed position, wherein the pinching surface is located at a height positioned above a height of the legs of the plurality of staples.

8. An apparatus, the apparatus comprising:
(a) a body assembly;
(b) a shaft extending distally from the body assembly;
(c) an end effector attached to the shaft, wherein the end effector comprises:
   (i) a jaw, and
   (ii) an anvil pivotable from an open position to a closed position relative to the jaw, wherein the anvil comprises a lateral edge located at a first lateral position; and
(d) a cartridge removably attached to the jaw, wherein the cartridge comprises:
   (i) a deck comprising an upper surface configured to face toward the anvil in the closed position, wherein the deck defines a plurality of openings,
   (ii) a plurality of staples located within the plurality of openings, wherein each staple in the plurality of staples comprises a pair of legs extending above the upper surface of the deck,
   (iii) a compressible buttress located on the upper surface of the deck, wherein portions of the legs of the staples are positioned in compressible buttress, and
   (iv) a pinching surface located adjacent to the compressible buttress, wherein the pinching surface extends to a height located above a height of the legs of the staples, wherein the first lateral position of the lateral edge shares a common lateral position with the pinching surface such that the lateral edge is configured to be laterally offset from the compressible buttress when the anvil is in the closed position.

* * * * *